(12) United States Patent
Braga et al.

(10) Patent No.: US 11,744,829 B2
(45) Date of Patent: *Sep. 5, 2023

(54) METHODS FOR TREATING NEUROLOGICAL CONDITIONS AND EXPOSURE TO NERVE AGENTS

(71) Applicant: The Henry M. Jackson Foundation for the Advancement of Military Medicine, Inc., Bethesda, MD (US)

(72) Inventors: Maria F. Braga, Bethesda, MD (US); Vassiliki Aroniadou-Anderjaska, Bethesda, MD (US)

(73) Assignee: The Henry M. Jackson Foundation for the Advancement of Military Medicine, Inc., Bethesda, MD (US)

( * ) Notice: Subject to any disclaimer, the term of this patent is extended or adjusted under 35 U.S.C. 154(b) by 190 days.

This patent is subject to a terminal disclaimer.

(21) Appl. No.: 17/360,912

(22) Filed: Jun. 28, 2021

(65) Prior Publication Data
US 2021/0393615 A1 Dec. 23, 2021

Related U.S. Application Data

(63) Continuation of application No. 16/309,898, filed as application No. PCT/US2017/036816 on Jun. 9, 2017, now Pat. No. 11,045,462.

(60) Provisional application No. 62/349,819, filed on Jun. 14, 2016.

(51) Int. Cl.
| | |
|---|---|
| *A61K 31/215* | (2006.01) |
| *A61K 31/472* | (2006.01) |
| *A61K 31/551* | (2006.01) |
| *A61P 25/22* | (2006.01) |
| *A61P 25/24* | (2006.01) |
| *A61P 39/02* | (2006.01) |
| *A61K 31/4725* | (2006.01) |
| *A61K 31/015* | (2006.01) |
| *A61K 31/216* | (2006.01) |
| *A61K 31/41* | (2006.01) |
| *A61K 31/5517* | (2006.01) |
| *A61K 45/06* | (2006.01) |

(52) U.S. Cl.
CPC ........ *A61K 31/4725* (2013.01); *A61K 31/015* (2013.01); *A61K 31/216* (2013.01); *A61K 31/41* (2013.01); *A61K 31/5517* (2013.01); *A61K 45/06* (2013.01)

(58) Field of Classification Search
CPC .. A61K 31/215; A61K 31/472; A61K 31/551; A61P 25/22; A61P 25/24; A61P 39/02
USPC ........................................ 514/221, 307, 530
See application file for complete search history.

(56) References Cited

U.S. PATENT DOCUMENTS

| | | | |
|---|---|---|---|
| 5,385,903 | A | 1/1995 | Steppuhn et al. |
| 11,045,462 | B2 | 6/2021 | Braga et al. |
| 2005/0153956 | A1 | 7/2005 | Merkus |
| 2010/0099714 | A1 | 4/2010 | Yoshino et al. |
| 2012/0232025 | A1 | 9/2012 | Olney |
| 2012/0264741 | A1 | 10/2012 | Volvovitz |
| 2015/0133488 | A1 | 5/2015 | Deftereos et al. |

FOREIGN PATENT DOCUMENTS

WO WO-2012/075286 A2 6/2012

OTHER PUBLICATIONS

Figueiredo et al., "Neuroprotective efficacy of caramiphen against soman and mechanisms of its action," British Journal of Pharmacology, vol. 164, pp. 1495-1505 (2011).
Me, "Inhibition by ketamine of muscarinic acetylcholine receptor function," Anesthesia & Analgesia, vol. 81, No. 1, pp. 57-62 (Jul. 1995).
Miller et al., "A rat model of nerve agent exposure applicable to the pediatric population: The anticonvulsant efficacies of atropine and GluK1 antagonists," Toxicol Appl Pharmacol., vol. 284, No. 2, pp. 204-216 (Apr. 2015).

*Primary Examiner* — Raymond J Henley, III
(74) *Attorney, Agent, or Firm* — Foley & Lardner LLP

(57) ABSTRACT

Described are methods of treating or reducing the toxic effects of exposure to a nerve agent, comprising administering to a subject in need thereof (i) an AMPA/GluR5 (GluK1) kainate receptor antagonist (such as LY293558) and (ii) an NMDA receptor antagonist (such as an antimuscarinic compound, such as caramiphen), as well as methods of treating, reducing the risks of, or preventing a neurological condition such as epilepsy, seizures, post-traumatic stress disorder, status epilepticus, depression, or anxiety, comprising administering to a subject in need thereof (i) an AMPA/GluR5(GluK1) kainate receptor antagonist (such as LY293558) and (ii) an NMDA receptor antagonist (such as an antimuscarinic compound, such as caramiphen). The methods may further comprise administering a positive allosteric modulator of synaptic $GABA_A$ receptors, such as a benzodiazepine, such as midazolam, to the subject. The methods are suitable for use in children and adults. Related compositions and uses also are described.

17 Claims, 25 Drawing Sheets

COMBINATION OF LY293558 AND CRM SIGNIFICANTLY INCREASED SURVIVAL RATE IN P21 RATS EXPOSED TO 1.2X LD50 SOMAN COMPARED TO ANIMALS THAT RECEIVED ONLY CRM AND TO LY293558-TREATED ANIMALS

SURVIVAL

| | SOMAN+CRM | SOMAN+LY293558 | SOMAN+BOTH |
|---|---|---|---|
| SURVIVAL 24H % | 64.6 | 87.5% | 95% |
| # OF RATS | 42/65 | 35/40 | 38/40 |

FIG. 5A

COMBINATION OF LY293558 AND CRM SIGNIFICANTLY REDUCES THE LATENCY TO STOP SEIZURES IN P21 RATS EXPOSED TO 1.2X LD50 SOMAN COMPARED TO LY293558-TREATED ANIMALS

SEIZURE CONTROL

| | SOMAN+CRM | SOMAN+LY293558 | SOMAN+BOTH |
|---|---|---|---|
| SEIZURE CONTROL % | 0 | 100% | 100% |
| # OF RATS | 0/65 | 40/40 | 40/40 |
| LATENCY TO SEIZURE CONTROL | -- | 25±3 MIN | 13 ±4 MIN * |

FIG. 5B

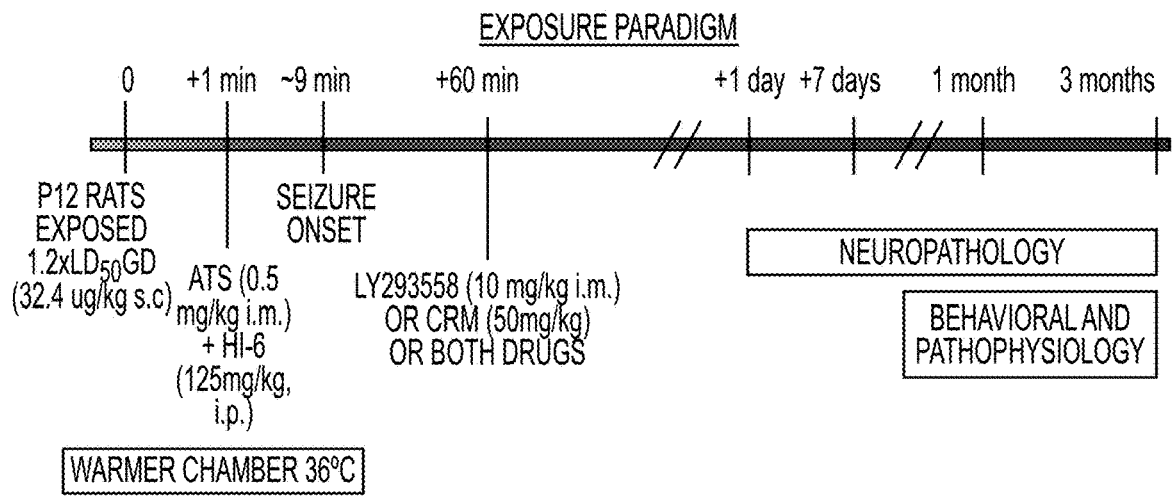

FIG. 21A

THE COMBINATION OF LY293558+CRM OR LY293558 ALONE SIGNIFICANTLY INCREASED SURVIVAL RATE IN P12 RATS EXPOSED TO 1.2X LD50 SOMAN COMPARED TO ANIMALS THAT RECEIVED ONLY CRM

SURVIVAL

|  | SOMAN+CRM | SOMAN+LY293558 | SOMAN+BOTH |
|---|---|---|---|
| SURVIVAL 24h % | 66.6% | 100%*** | 100%*** |
| # OF RATS | 16/24 | 18/18 | 18/18 |

*** $P<0.001$ FISHER EXACT PROBABILITY TEST

FIG. 21B

THE COMBINATION OF LY293558+CRM SIGNIFICANTLY REDUCES THE LATENCY TO STOP SEIZURES IN P12 RATS EXPOSED TO 1.2X LD50 SOMAN COMPARED TO LY293558-TREATED ANIMALS

SEIZURE CONTROL

|  | SOMAN+CRM | SOMAN+LY293558 | SOMAN+BOTH |
|---|---|---|---|
| SEIZURE CONTROL % | 0 | 100% | 100% |
| # OF RATS | 0/18 | 18/18 | 18/18 |
| LATENCY TO SEIZURE CONTROL | -- | 35±6 MIN | 18±5 MIN * |

*$p<0.05$ T-TEST

FIG. 21C

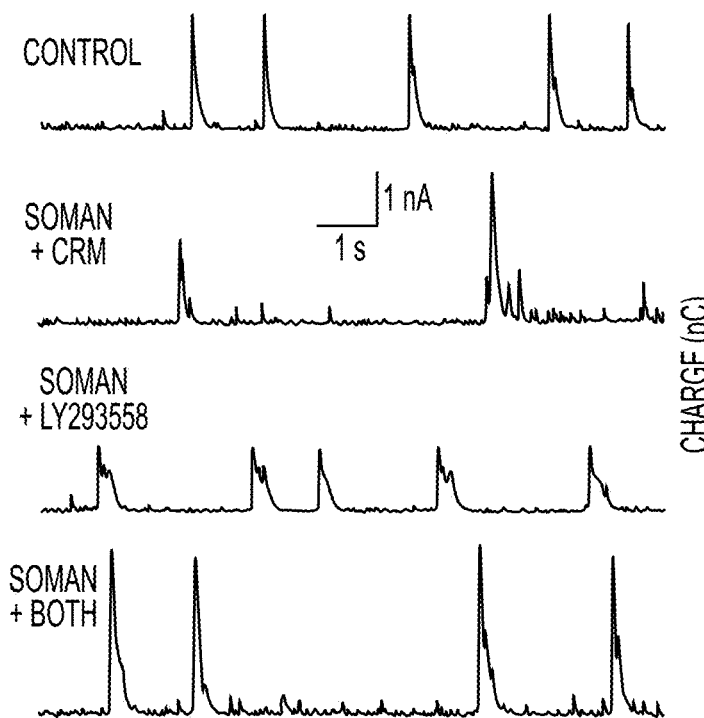
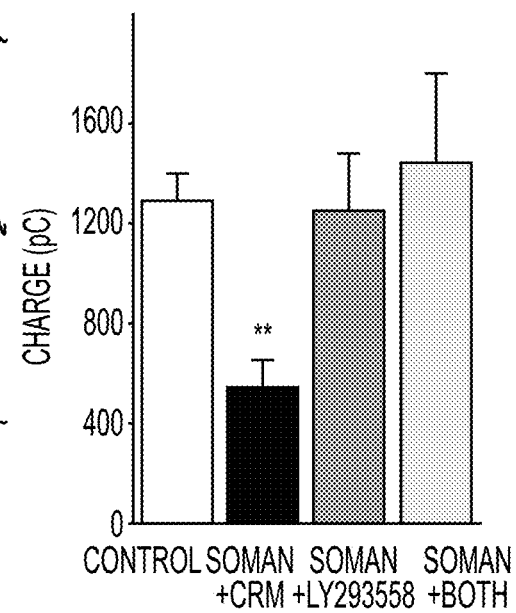
FIG. 24A          FIG. 24B

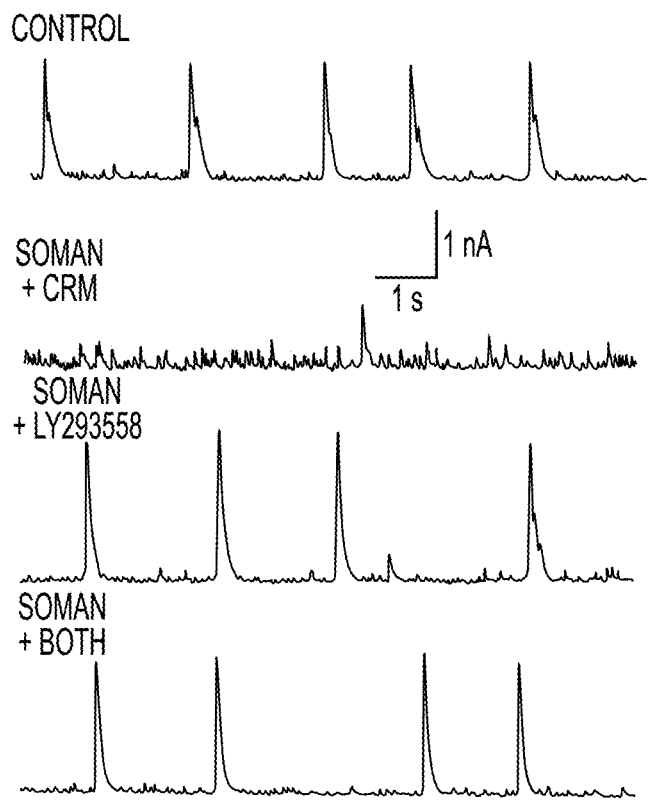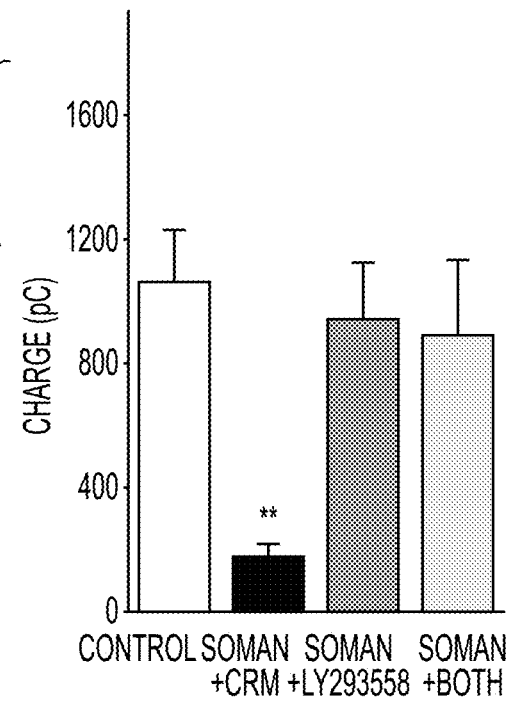
*FIG. 26A*  *FIG. 26B*

METHODS FOR TREATING NEUROLOGICAL CONDITIONS AND EXPOSURE TO NERVE AGENTS

CROSS-REFERENCE TO RELATED APPLICATIONS

The present application is a continuation of U.S. application Ser. No. 16/309,898, filed on Dec. 13, 2018, now U.S. Pat. No. 11,045,462, which is the U.S. National Stage of International Application No. PCT/US2017/036816 filed Jun. 9, 2017, and claims priority to U.S. Provisional Patent Application No. 62/349,819, filed Jun. 14, 2016.

GOVERNMENT RIGHTS

This invention was made with government support under NS094131 awarded by National Institutes of Health. The government has certain rights in the invention."

FIELD

The present disclosure relates generally to the field of treating neurological conditions, including neurological conditions triggered by exposure to nerve agents, including seizures. Described are methods comprising administering to a subject in need thereof (i) at least one AMPA/GluR5 (GluK1) kainate receptor antagonist and (ii) at least one NMDA receptor antagonist. In some embodiments, the methods further comprise administering a positive allosteric modulator of synaptic $GABA_A$ receptor), such as a benzodiazepine, such as midazolam. The neurological conditions that can be treated include, but are not limited to epilepsy, seizures (e.g., refractory seizures; seizures caused by exposure to nerve agents, such as organophosphorus nerve agents including soman and sarin; seizures caused by chemical (e.g. alcohol or opiate) withdrawal; etc.), post-traumatic stress disorder (PTSD), status epilepticus (SE), depression, and anxiety.

BACKGROUND

The following discussion is merely provided to aid the reader in understanding the disclosure and is not admitted to describe or constitute prior art thereto.

Many neurological conditions, such as epilepsy, seizures, post-traumatic stress disorder (PTSD), status epilepticus (SE), depression, and anxiety are caused by aberrant chemical signaling in the brain or central nervous system (CNS). In particular, signaling through α-amino-3-hydroxy-5-methyl-4-isoxazolepropionic acid receptors (AMPA receptors), kainate receptors (KARs, which are ionotropic receptors made up of five types of subunits including GluR5 (GluK1), GluR6, GluR7, KA1, and KA2), and N-methyl-D-aspartate receptor (NMDA receptors) can play a role in each of these conditions. Nerve agents and other organophosphorus compounds may interfere with these same signaling pathways.

Nerve agents such as organophosphorus nerve agents are potent toxins that act primarily by inhibiting the activity of acetylcholinesterase. The resulting accumulation of acetylcholine at synaptic junctions produces peripheral cholinergic crisis (excessive salivation, lacrimation, rhinorrhea, bronchorrhea, cardiorespiratory suppression, eventual muscle paralysis, etc.), and induces seizures and status epilepticus (SE), resulting in brain damage and death. The possibility that nerve agents can be employed by terrorists to inflict mass casualties necessitates readiness on the part of the government to protect the people, including the more vulnerable sections of the population, including children. The devastating effects of the sarin attack in Syria in August of 2013, where 1,400 civilians were killed, 426 of which were children, underscored the need for effective treatments to save lives and protect against long-term health consequences of exposure to nerve agents.

It is generally understood that during seizures, including seizures induced by nerve agents, GABAergic and glutamatergic activity are out of balance, with a strong dominance of the latter. Without wanting to be bound by theory, it is believed that initiation of seizures (e.g., seizures caused by nerve agent exposure) is due to excessive elevation of acetylcholine—secondarily to AChE inhibition—acting primarily on muscarinic receptors, but that seizures are sustained and reinforced by glutamatergic rather than cholinergic mechanisms.

One way to suppress glutamatergic hyperactivity is by enhancing GABAergic inhibition. Accordingly, benzodiazepines, which are positive allosteric modulators of $GABA_A$ receptors, have long been the first line of treatment to induce cessation of SE triggered by various etiologies, including nerve agents. The benzodiazepine diazepam (DZP) is currently the only FDA-approved injectable drug for the control of seizures caused by nerve agents. However, the efficacy of benzodiazepines decreases significantly as the time between initiation of SE and treatment increases. This represents a significant drawback in the context of SE and other conditions involving unpredictable seizures, including seizures induced by nerve agents, because it may be difficult or impossible to administer treatment promptly, such as after exposure to nerve agents caused by a terrorist attack or after another seizure-triggering event.

Benzodiazepines also may become less effective over time, e.g., a tolerance to benzodiazepines may develop, in which case seizures may recur. Additionally, while DZP has been used for adults, it may not be suitable for use in children. For example, there is evidence suggesting that immature animals differ from adult animals both in seizure susceptibility and in the extent and nature of neuropathology that seizures can induce. The American Academy of Pediatrics have announced that mass casualties during terrorist attacks that employ nerve agents are expected to disproportionately affect children due to their greater body surface area-to-body mass ratio, increased skin permeability, faster respiration rate, breathing at a level where nerve agent vapor density would be highest, and an increased susceptibility to seizures. Although the American Academy of Pediatrics has identified reasons why children are more vulnerable to nerve agent toxicity, there is very little information on the appropriate countermeasures for use in the pediatric population.

Aberrant biochemical signaling in the brain and CNS also can lead to epilepsy, depression, anxiety, and related conditions. Hyperexcitability of the amygdala is a characteristic of depression, anxiety disorders, and PTSD, and hyperexcitability of the basolateral nucleus of the amygdala (BLA) may be particularly important in this regard. The BLA has a remarkably high expression of GluK1 kainate receptors (GluK1KRs), which can impact the modulation of GABAergic and glutamatergic transmission in the BLA. Indeed, the net effect of GluK1KR activation is to increase excitability, and therefore blockade of GluK1KRs in the BLA can produce anxiolytic effects. Likewise, depressive patients are known to respond to NMDAR antagonists and there is some evidence in rats suggesting that inhibition of this receptor can produce antidepressant effects. Yet, depression, anxiety, and anxiety-related disorders continue to be a pressing problems in the health system of the United States and abroad.

Accordingly, there is a need for effective methods of treating neurological conditions, such as epilepsy, various types of seizures, post-traumatic stress disorder (PTSD), status epilepticus, depression, and anxiety, including methods that may be suitable for use in children.

SUMMARY

Described herein are methods for treating neurological conditions, including methods for treating or reducing the toxic effects of exposure to nerve agents.

For instance, in one aspect, the present disclosure relates to methods of treating or reducing the toxic effects of exposure to a nerve agent, comprising administering to a subject in need thereof (i) an AMPA/GluR5(GluK1) kainate receptor antagonist and (ii) an NMDA receptor antagonist.

In another aspect, the present disclosure relates to methods of treating or reducing the risks of a neurological condition, comprising administering to a subject in need thereof (i) an AMPA/GluR5(GluK1) kainate receptor antagonist and (ii) an NMDA receptor antagonist. In some embodiments, the neurological condition may be, for example, epilepsy, seizure, post-traumatic stress disorder, status epilepticus, depression, or anxiety.

In some embodiments, the AMPA/GluR5(GluK1) kainate receptor antagonist is LY293558.

In some embodiments, the NMDA receptor antagonist is an antimuscarinic compound like, for example, caramiphen.

In some embodiments, the disclosed methods may further comprise administering a positive allosteric modulator of synaptic $GABA_A$ receptors to the subject. In some embodiments, the positive allosteric modulator of synaptic $GABA_A$ receptors is a benzodiazepine, for example, midazolam.

In some embodiments, the AMPA/GluR5(GluK1) kainate receptor antagonist and the NMDA receptor antagonist, and, optionally, the positive allosteric modulator of synaptic $GABA_A$ receptors, are administered in the same composition.

In some embodiments, the AMPA/GluR5(GluK1) kainate receptor antagonist and the NMDA receptor antagonist, and, optionally, the positive allosteric modulator of synaptic $GABA_A$ receptors, are administered in separate compositions, by the same route of administration or by different routes of administration. For instance, the AMPA/GluR5(GluK1) kainate receptor antagonist and the NMDA receptor antagonist, and, optionally, the positive allosteric modulator of synaptic $GABA_A$ receptors, are administered substantially simultaneously. Alternatively, the AMPA/GluR5(GluK1) kainate receptor antagonist and the NMDA receptor antagonist, and, optionally, the positive allosteric modulator of synaptic $GABA_A$ receptors, are administered sequentially.

In some embodiments, the AMPA/GluR5(GluK1) kainate receptor antagonist is administered prior to the administration of the NMDA receptor antagonist. In some embodiments, the AMPA/GluR5(GluK1) kainate receptor antagonist is administered after to the administration of the NMDA receptor antagonist. In some embodiments, the positive allosteric modulator of synaptic $GABA_A$ receptors is administered prior to both the AMPA/GluR5(GluK1) kainate receptor antagonist and the NMDA receptor antagonist, after both the AMPA/GluR5(GluK1) kainate receptor antagonist and the NMDA receptor antagonist, or prior to one of the AMPA/GluR5(GluK1) kainate receptor antagonist and the NMDA receptor antagonist and after the other of the AMPA/GluR5(GluK1) kainate receptor antagonist and the NMDA receptor antagonist.

In some embodiments, the AMPA/GluR5(GluK1) kainate receptor antagonist and the NMDA receptor antagonist and, optionally, the positive allosteric modulator of synaptic $GABA_A$ receptors, are administered by injection like, for example, an intramuscular injection. In some embodiments, the AMPA/GluR5(GluK1) kainate receptor antagonist and the NMDA receptor antagonist and, optionally, the positive modulator of synaptic GABA-A receptors, are administered orally.

In some embodiments relating to treating or reducing the toxic effects of exposure to a nerve agent, the nerve agent comprises an organophosphorus toxin, such as soman or sarin. In some embodiments, the subject has been exposed to a nerve agent. In some embodiments, administration of the AMPA/GluR5(GluK1) kainate receptor antagonist and NMDA receptor antagonist occurs within 20 minutes or less, one hour or less, or two hours or less of exposure to the nerve agent. In some embodiments, the subject is suspected of having been exposed to a nerve agent. In some embodiments, the subject is at risk of exposure to a nerve agent. In some embodiments, the method is effective to treat or reduce the toxic effects of exposure to the nerve agent selected from one or more of seizures, status epilepticus, brain damage, neurological effects, behavioral effects, difficulty breathing, nausea, loss of control of bodily functions, and death.

In some embodiments related to treating or reducing the risks of a neurological condition, the neurological condition is a seizure such as a refractory seizure, an epileptic seizure, or a seizure induced by withdrawal from a chemical (e.g. alcohol or opiate). For example, when the seizure is induced by withdrawal from a chemical (e.g. alcohol or opiate), administration of the AMPA/GluR5(GluK1) kainate receptor antagonist and NMDA receptor antagonist, and, optionally, the positive allosteric modulator of synaptic $GABA_A$ receptors, may occur prior to withdrawal of the chemical, during detoxification of the subject, or after withdrawal of the chemical. In some embodiments, the subject has been diagnosed with the neurological condition. In some embodiments, the method is effective to treat or reduce signs or symptoms of the neurological condition.

In some embodiments, the disclosed methods further comprise at least one subsequent administration of the AMPA/GluR5(GluK1) kainate receptor antagonist and NMDA receptor antagonist and, optionally, the positive allosteric modulator of synaptic $GABA_A$ receptors. In some embodiments, the at least one subsequent administration is administered by injection, while in some embodiments, the at least one subsequent administration is administered orally.

In embodiments of any of the methods described herein, the subject may be a mammal, such as a human child or a human adult.

Also provided are an AMPA/GluR5(GluK1) kainate receptor antagonist and an NMDA receptor antagonist, and, optionally a positive allosteric modulator of synaptic $GABA_A$, as described herein, for treating or reducing the toxic effects of exposure to a nerve agent.

Also provided are an AMPA/GluR5(GluK1) kainate receptor antagonist and an NMDA receptor antagonist, and, optionally a positive allosteric modulator of synaptic $GABA_A$, as described herein, for treating or reducing the risks of a neurological condition.

Also provided are uses of (i) an AMPA/GluR5(GluK1) kainate receptor antagonist and (ii) an NMDA receptor antagonist, and, optionally a positive allosteric modulator of synaptic $GABA_A$, as described herein, in the preparation of one or more medicaments as described herein for treating or reducing the toxic effects of exposure to a nerve agent as described herein, or for treating or reducing the risks of a neurological condition as described herein.

The foregoing general description and following detailed description are exemplary and explanatory and not limiting of the invention.

BRIEF DESCRIPTION OF DRAWINGS

FIG. 1A shows the time course of seizure suppression by LY293558, while FIG. 1B shows the time course of seizure suppression by LY293558+CRM. FIG. 1C illustrates electrode placement (1, 2, 3, 4) where electrical activity was sampled (1: left frontal; 2: right frontal; 3: left parietal; 4: right parietal; un-labeled: cerebellar reference electrode). FIG. 1D, left panel, shows the duration of the initial SE, which is the SE that started within 6-10 min after soman exposure and was terminated by 15 mg/kg LY293558 (open bar), or 15 mg/kg LY293558 and 50 mg/kg CRM (closed bar). FIG. 1D, right panel, shows the duration of SE throughout the 7 day-period after soman exposure for the same two groups. The corresponding durations for the untreated soman group (not shown) are about 700 min for the initial SE and more than 1000 min for the 7-day-period. *$p<0.05$ (Unequal Variance t-test).

FIGS. 2A and 2B show panoramic photomicrographs of Nissl-stained sections showing the brain regions from the Fluoro-Jade C photomicrographs displayed in FIG. 2C. FIG. 2C shows representative photomicrographs of Fluoro-Jade C stained sections from the brain regions where neuronal degeneration was evaluated, for the untreated (SOMAN), LY293558-treated (SOMAN+ LY293558) and LY293558- and CRM-treated (SOMAN+ LY293558+CRM) groups. Total magnification is 100×. Scale bar is 50 µm. FIG. 2D shows median neuropathology score and interquartile range for the amygdala (Amy), piriform cortex (Pir), entorhinal cortex (Ent), the CA1 and CA3 subfields of the ventral hippocampus, hilus, and neocortex (neo-Ctx).

FIG. 4A shows time spent in the center of the open field, which was significantly reduced only in the group treated with CRM alone. FIG. 4B shows that there was no effect on the total distance travelled. FIG. 4C shows that acoustic startle responses to both 110 dB and 120 dB acoustic stimuli were significantly increased only in the group treated with CRM alone. *$p<0.05$ compared to Control (One Way ANOVA, Dunnett post-hoc), n=8~12 rats/group.

FIGS. 5A-5B show increased survival rate and seizure control in animals treated by the present methods. FIG. 5A shows that treatment with LY293558 and CRM significantly increased the survival rate of 21 day old rats exposed to $1.2 \times LD_{50}$ of soman (74.4 µg/kg), as compared to animals treated with only one of LY293558 or CRM. FIG. 5B shows that treatment with LY293558 and CRM significantly reduced the time to stop seizures in 21 day old rats exposed to $1.2 \times LD_{50}$ of soman, as compared to animals treated with only one of LY293558 or CRM.

FIG. 7A shows tracings of the amygdala in series of slices (left) and representative photomicrographs (middle) from control animals (n=7), soman-exposed animals that received CRM (50 mg/kg) at 60 minutes post-exposure (n=10), soman-exposed animals that received LY293558 (20 mg/kg) at 60 minutes after soman-injection (n=10) and soman-exposed animals that received both LY293558 and CRM at 60 minutes after soman-injection (n=10). FIG. 7B shows group data showing the estimated volume of the amygdala for all three groups, 30 days after the exposure (top) and 3 months after the exposure (bottom). * $p<0.05$.

FIG. 8A shows tracings of the hippocampus in series of slices (left) and representative photomicrographs (right) from control animals (n=7), soman-exposed animals that received CRM (n=7), and soman-exposed animals that received LY293558 (20 mg/kg) at 1 hour after soman injection (n=8). FIG. 8B shows group data showing the estimated volume of the hippocampus for all three groups, 30 days after the exposure, and group data showing the estimated volume of the hippocampus for all three groups, 90 days after the exposure. *$p<0.05$.

FIG. 17A shows observations of total SE over 24 hours, for soman (n=4), soman+DZP (n=6) and soman+UBP302 (n=8). FIG. 17B shows observations of total SE over 24 hours, for soman (n=4), soman+DZP (n=4) and soman+UBP302 (n=4), * $p<0.05$,  $p<0.01$ and * $p<0.001$ by ANOVA and post-hoc testing.

FIG. 20A and FIG. 20B: Observations are n=10 for each group. FIG. 20C: Observations are n=16 for Control, n=7 for Midazolam and n=5 for LY293558. FIG. 20A: Percent of Time Spent in the Center of the Open Field test. FIG. 20B: Startle Response amplitude measured during Acoustic Startle Response test. FIG. 20C: Charge (in pico-Coulombs; pC) transferred by GABA-A receptor-mediated spontaneous Inhibitory Postsynaptic Currents (sIPSCs) recorded from BLA principal neurons during 10 s time window. *$p<0.05$, One-Way ANOVA with Dunnett's T post hoc.

FIGS. 21A-21C show increased survival rate and seizure control in newborn animals treated with LY293558 and CRM. FIG. 21 A shows the experimental protocol for newborn animals. FIG. 21B shows that treatment with LY293558 and CRM significantly increased the survival rate of 12 day old rats exposed to $1.2 \times LD_{50}$ of soman (32.4 µg/kg), as compared to animals treated with only CRM. FIG. 21C shows that treatment with LY293558 and CRM significantly reduced the time to stop seizures in 12 day old rats exposed to $1.2 \times LD_{50}$ of soman, as compared to animals treated with only one of LY293558 or CRM.

FIG. 22A shows an animal from SOMAN group showing a spontaneous recurrent seizure (behavioral correlates, rearing and falling). FIG. 22B shows an animal from SOMAN+LY293558 group with presence of spontaneous epileptiform discharges. FIG. 22C shows an animal from SOMAN+LY293558+CRM with normal EEG.

FIGS. 23A-23B show percent time spent in the center of the open field (A) and distance travelled (B). FIG. 23C shows startle response amplitude for the control group (n=9), soman-exposed rats who received CRM (n=8), similarly treated rats who received LY293558 at 60 min after soman exposure (n=9), and for rats who received the combination of LY293558 and CRM (n=9). * $p<0.05$ compared to Control group, ANOVA Dunnett post-hoc test.

FIGS. 24A-24B show LY293558 or combination of LY293558 and caramiphen prevented the reduction in charge transferred by $GABA_A$ receptor-mediated spontaneous IPSCs, 30 days after exposure to soman in P12 rats. FIG. 24A shows example current traces in v-clamp mode. $GABA_A$ receptor-mediated sIPSCs were recorded at +30 mV holding potential. FIG. 24B shows charge [pico-Coulombs; pC] transferred by sIPSCs of BLA principal neurons during 10 s time window, 30 days after soman exposure. N=8~20 cells/group ** $p<0.05$ compared to Control group, ANOVA LSD post-hoc Test.

FIGS. 25A and 25B show percent time spent in the center of the open field (A) and distance travelled (B). FIG. 25C shows startle response amplitude for the control group (n=8), soman-exposed rats who received CRM (n=8), similarly treated rats who received LY293558 at 60 min after soman exposure (n=9), and for rats who received the combination of LY293558 and CRM (n=9). ** p<0.01 compared to Control group, ANOVA Dunnett post-hoc test.

FIGS. 26A-26B show LY293558 or combination of LY293558 and caramiphen prevented the reduction in charge transferred by $GABA_A$ receptor-mediated spontaneous IPSCs, 3 months after exposure to soman in P12 rats. FIG. 26A shows example current traces in v-clamp mode. $GABA_A$ receptor-mediated sIPSCs were recorded at +30 mV holding potential. FIG. 26B shows charge [pico-Coulombs; pC] transferred by sIPSCs of BLA principal neurons during 10 s time window, 30 days after soman exposure. N=8~20 cells/group ** p<0.05 compared to Control ANOVA LSD post-hoc Test.

DETAILED DESCRIPTION

Figures 1A, 1B, 1C, 1D:
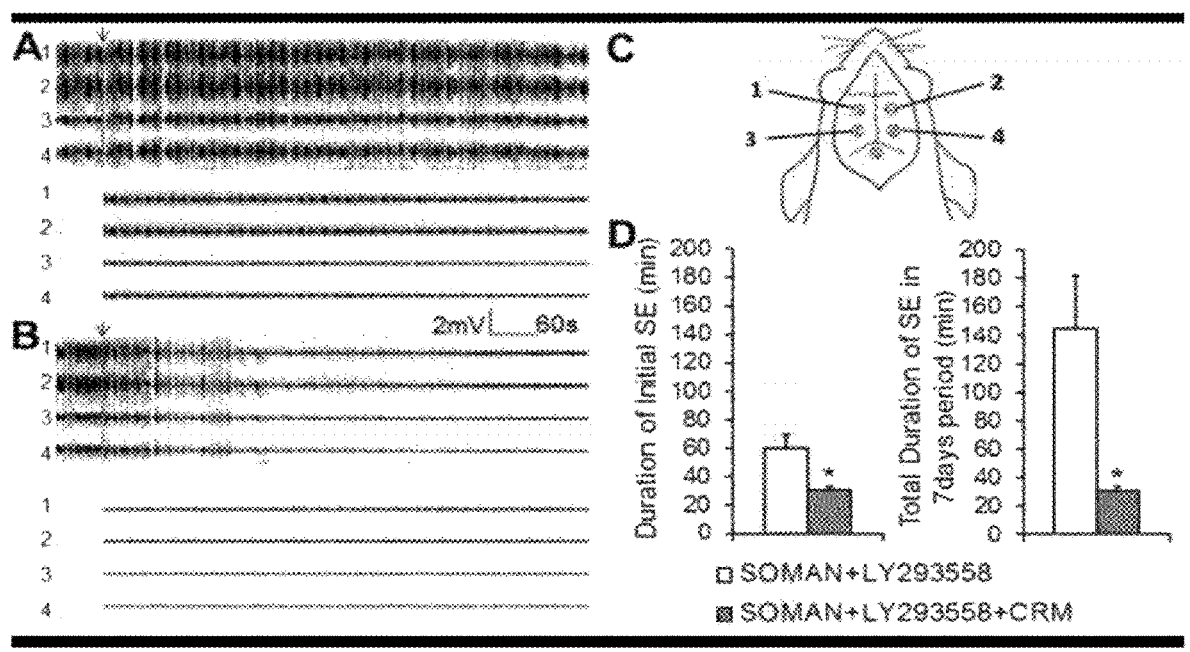
FIGS. 1A-D show the effect of the methods described herein in a rat model, using LY293558 as the AMPA/GluR5 (GluK1) kainate receptor antagonist and caramiphen (CRM) as the NMDA receptor antagonist to stop seizures induced by the nerve agent soman ($1.2 \times LD_{50}$, 132 µg/kg), where the method reduced the duration of the initial SE and the total duration of SE as compared to treatment with LY293558 alone.

Disclosed herein are methods of treating neurological conditions, and methods for treating or reducing the toxic effects of exposure to nerve agents, including seizures. The neurological conditions that may be treated in accordance with the methods described herein include epilepsy, various types of seizures (e.g., seizures caused by exposure to nerve agents, refractory seizures, seizures due to chemical (e.g. alcohol or opiate) withdrawal, etc.), post-traumatic stress disorder (PTSD), status epilepticus (SE), depression, and anxiety. The methods may comprise administering to a subject in need thereof (i) at least one AMPA/GluR5(GluK1) kainate receptor antagonist and (ii) at least one NMDA receptor antagonist. In some embodiments, the methods further comprise administering a positive allosteric modulator of synaptic $GABA_A$ receptors, such as a benzodiazepine, such as midazolam, to the subject. For instance, in one aspect, the present disclosure relates to methods of treating or reducing the toxic effects of exposure to a nerve agent, comprising administering to a subject in need thereof (i) an AMPA/GluR5(GluK1) kainate receptor antagonist and (ii) an NMDA receptor antagonist. In another aspect, the present disclosure relates to methods of treating or reducing the risks of a neurological condition, such as one or more selected from epilepsy, various types of seizures (e.g., seizures caused by exposure to nerve agents, refractory seizures, seizures due to chemical (e.g. alcohol or opiate) withdrawal, etc.), post-traumatic stress disorder (PTSD), status epilepticus (SE), depression, and anxiety, comprising administering to a subject in need thereof (i) an AMPA/GluR5(GluK1) kainate receptor antagonist and (ii) an NMDA receptor antagonist. The AMPA/GluR5(GluK1) kainate receptor antagonist may be LY293558. Independently, the NMDA receptor antagonist may be caramiphen (CRM). In any embodiments, the subject may further be administered a positive allosteric modulator of synaptic $GABA_A$ receptors, such as a benzodiazepine, such as midazolam. Also described are (i) a AMPA/GluR5(GluK1) kainate receptor antagonist and (ii) an NMDA receptor antagonist, and, optionally, a positive allosteric modulator of synaptic $GABA_A$ receptors, for treating or reducing the toxic effects of exposure to a nerve agent, or for treating or reducing the risks of a neurological condition. Also described are uses of such agents in the preparation of one or more medicaments for treating or reducing the toxic effects of exposure to a nerve agent, or for treating or reducing the risks of a neurological condition.

In subjects exposed to or at risk of exposure to a nerve agent, the methods or uses may be effective to treat, prevent, reduce, ameliorate, or eliminate the effects of exposure to a nerve agent, such as seizures, brain damage, behavioral deficits, pathophysiological alterations in brain regions that underlie these deficits, and death. In subjects suffering from a neurological condition, the methods or uses may be effective to treat, prevent, reduce, ameliorate, or eliminate the effects of the neurological condition, such as seizures, brain damage, behavioral deficits, pathophysiological alterations in brain regions that underlie these deficits, and death.

The inventor discovered that treating subjects suffering from a neurological condition and/or exposed to nerve agents with both (i) an AMPA/GluR5(GluK1) kainate receptor antagonist such as LY293558 and (ii) an NMDA receptor antagonist such as CRM achieved synergistic results with regard to therapeutic efficacy. In the context of treating exposure to nerve agents, the described methods have been shown to be superiorly efficacious not only in stopping seizures very rapidly, but also in preventing brain damage, behavioral deficits, and resulting in very quick recovery.

Definitions

Technical and scientific terms used herein have the meanings commonly understood by one of ordinary skill in the art, unless otherwise defined. Any suitable materials and/or methodologies known to those of ordinary skill in the art can be utilized in carrying out the methods described herein.

As used in the description of the invention and the appended claims, the singular forms "a", "an" and "the" are used interchangeably and intended to include the plural forms as well and fall within each meaning, unless the context clearly indicates otherwise. Also, as used herein, "and/or" refers to and encompasses any and all possible combinations of one or more of the listed items, as well as the lack of combinations when interpreted in the alternative ("or").

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

As used herein, the phrase "therapeutically effective amount" means a dose that provides the specific pharmacological effect for which the compound or compounds are being administered. It is emphasized that a therapeutically effective amount will not always be effective in achieving the intended effect in a given subject, even though such dose is deemed to be a therapeutically effective amount by those of skill in the art. For convenience only, exemplary dosages are provided below. Those skilled in the art can adjust such amounts in accordance with standard practices as needed to treat a specific subject. The therapeutically effective amount may vary based on the route of administration and dosage form, the age and weight of the subject, and/or the subject's condition. For example one of skill in the art would understand that the therapeutically effective amount for treating depression, anxiety, or PTSD may be different from the therapeutically effective amount for treating acute exposure to a nerve agent. In the context of treating exposure to a nerve agent, the type and amount of nerve agent exposure, and the amount of time that has passed between exposure and administration of a treatment may have a bearing on the dose needed to therapeutically effective.

The terms "treatment" or "treating" as used herein includes preventing, reducing, ameliorating, or eliminating one or more symptoms or effects of the neurological condition being treating, or of exposure to a nerve agent.

The term "administering" as used herein includes prescribing for administration as well as actually administering, and includes physically administering by the subject being treated or by another.

As used herein "subject" or "individual" refers to any subject or individual, such as a subject suffering from a neurological condition or a subject that has been exposed to or is at risk of being exposed to a nerve agent, such as soman or sarin, and the terms are used interchangeably herein. In this regard, the terms "subject" and "individual" includes mammals, and, in particular humans.

As used herein, "child" generally refers to a human subject up to about 18 years of age. As used herein, a child can be a subject who begins a course of treatment prior to turning about 18 years of age, even if the subject continues treatment beyond 18 years of age. In specific embodiments, a child may be less than 1 year old, less than 2 years old, less than 3 years old, less than 4 years old, less than 5 years old, less than 6 years old, less than 7 years old, less than 8 years old, less than 9 years old, less than 10 years old, less than 11 years old, less than 12 years old, less than 13 years old, less than 14 years old, less than 15 years old, less than 16 years old, less than 17 years old, or less than 18 years old.

Therapeutic Compounds

The disclosed methods are effective for treating or reducing the toxic effects of exposure to a nerve agent and for treating neurological conditions, including epilepsy, various types of seizures, PTSD, SE, depression, and anxiety. The disclosed methods comprise administering (i) an AMPA/GluR5(GluK1) kainate receptor antagonist and (ii) an NMDA receptor antagonist. The AMPA/GluR5(GluK1) kainate receptor antagonist may be LY293558. Independently, the NMDA receptor antagonist may be caramiphen (CRM). In some embodiments, the methods further comprise administering a positive allosteric modulator of synaptic $GABA_A$ receptors, such as a benzodiazepine, such as midazolam, to the subject.

In subjects exposed to or at risk of exposure to a nerve agent, the methods may be effective to treat, prevent, reduce, ameliorate, or eliminate the effects of exposure to a nerve agent, such as seizures, brain damage, and the consequences on behavior, pathophysiological alterations in brain regions that underlie these deficits, and death. In subjects suffering from a neurological condition, the methods may be effect to treat, prevent, reduce, ameliorate, or eliminate the effects of the neurological condition, such as seizures, brain damage, behavioral deficits, pathophysiological alterations in brain regions that underlie these deficits, and death.

The methods described herein exclusively target the glutamatergic system with at least two separate active agents, providing a new therapeutic approach to treat exposure to nerve agents and neurological conditions; and may be particularly suitable for treating children. Indeed, the methods described herein represent the only therapy that has the potential to fully succeed in treating both children and adults intoxicated with nerve agents or suffering from other neurological conditions discussed herein. This is because, in the brain of a child, the GABAergic inhibitory system is not fully developed, and its activation (or facilitation, such as promoted by benzodiazepines such as diazepam or midazolam) may produce depolarization and excitation instead of inhibition. For similar reasons, the disclosed methods provide a new therapeutic approach to treating, reducing the risks of, or preventing epilepsy, various types of seizures (e.g., seizures due to exposure to a nerve agent, refractory seizures, seizures due to opiate withdrawal, etc.), PTSD, SE, depression, and anxiety. These conditions may also be treated with the disclosed therapeutic combinations in both children and adults. Thus, the methods described herein avoid those effects and so can be used to effectively treat nerve agent exposure and neurological conditions in both children and adults.

As noted above, the AMPA/GluR5(GluK1) kainate receptor antagonist may be LY293558 (also known as Tezampanel). LY293558 ((3S,4aR,6R,8aR)-6-[2-(1(2)H-tetrazole-5-yl) ethyl]decahydroisoquinoline-3-carboxylic acid) is an antagonist of the α-amino-3-hydroxy-5-methyl-4-isoxazole-propionic acid receptor (AMPA receptor) and kainate receptors containing the GluR5 (GluK1) kainate subunit (GluR5KRs).

As also noted above, the NMDA receptor antagonist may be caramiphen (CRM). Caramiphen (CRM) is an antagonist of the N-methyl-D-aspartate (NMDA) receptor with anticholinergic properties. CRM has a good safety record in humans, including children. CRM was approved by the FDA in 1973 as an over-the-counter antitussive for human use from the age of two years and above. The FDA approval was withdrawn in 1984 due to its lack of efficacy as an antitussive but not because of safety concerns.

While caramiphen may be used in some embodiments, other NMDA receptor antagonists also are suitable for use in the methods described herein, including other NMDA receptor antagonists with or without antimuscarinic activity, including, but not limited to, APV (R-2-amino-5-phosphonopentanoate), AP7 (2-amino-7-phosphonoheptanoic acid), CPPene (3-[(R)-2-carboxypiperazin-4-yl]-prop-2-enyl-1-phosphonic acid), Selfotel, Amantadine, Atomoxetine, Agmatine, Chloroform, Dextrallorphan, Dextromethorphan, Dextrorphan, Diphenidine, Dizocilpine (MK-801), Ethanol, Eticyclidine, Gacyclidine, Ibogaine, Magnesium, Memantine, Methoxetamine, Nitromemantine, Nitrous oxide, Phencyclidine, Rolicyclidine, Tenocyclidine, Methoxydine, Tiletamine, Neramexane, Eliprodil, Etoxadrol, Dexoxadrol, WMS-2539, NEFA, Remacemide, Delucemine, 8A-PDHQ, Aptiganel (Cerestat, CNS-1102, HU-211, Rhynchophylline, and Ketamine.

Methods using both of these types of therapeutic compounds (an AMPA/GluR5(GluK1) kainate receptor antagonist and NMDA receptor antagonist) to treat exposure to nerve agents are particularly advantageous and show a synergistic increase in therapeutic effect as compared to treatment with only one or the other. Thus, using both types of therapeutic compounds permits the dose of each to be considerably lower than would be required if a compound were being used individually, thus decreasing the risks of side effects and increasing the tolerability of the treatment protocol in humans. In the discussion that follows, the AMPA/GluR5(GluK1) kainate receptor antagonist and NMDA receptor antagonist are referred to collectively as the "therapeutic compounds." In some embodiments, the methods may further comprise administering a positive allosteric modulator of synaptic $GABA_A$ receptors, such as a benzodiazepine, such as midazolam, to the subject, in addition to the AMPA/GluR5(GluK1) kainate receptor antagonist and NMDA receptor antagonist (e.g., LY293558 and caramiphen, respectively). While not wanting to be bound by theory, it is believed that benzodiazepines such as midazolam exert anticonvulsant activity by enhancing inhibitory GABAergic transmission through an increase in the channel opening frequency of the $GABA_A$ receptors, a subsequent increase in chloride conductance, and neuronal hyperpolarization. Midazolam is a benzodiazepine compound, and is a powerful anticonvulsant, sedative, and anxiolytic compound, and a first-line therapy for acute seizures and status epilepticus. It has a short half-life and rapid onset of action when administered intravenously or intramuscularly to control acute repetitive seizures and SE. Midazolam has an elimination half-life of 1.5-2.5 hours in adults, and a longer half-life in the elderly and young children. Midazolam may be administered orally, buccally, nasally, intravenously, or intramuscularly.

Midazolam has been considered a better anticonvulsant than diazepam for nerve agent-induced seizures due to its improved water solubility which provides increased product stability and faster absorption. However, like diazepam, midazolam shows diminishing efficacy against nerve agent-induced seizures and SE with delayed administration (such as greater than 40 minutes after nerve agent exposure).

Embodiments using therapeutic compounds from these three categories (such as LY293558, caramiphen and midazolam) will be particularly efficacious because each exerts activity via a different mechanism of action, and so their use in combination may yield synergistic results. For example, in the context of treating, reducing the risks of, or preventing seizures, including seizures induced by exposure to nerve agents, each exert anticonvulsant activity via a different mechanism of action, fostering a synergistic effect that will greatly reduce hyperexcitability in the brain and effectively stop the seizures and SE. In addition, embodiments using therapeutic compounds from these three categories will permit the dose of each compound to be considerably lower than would be required if a compound were being used individually, or in conjunction with only one other compound, thus decreasing the risks of side effects and increasing the tolerability of the treatment protocol in humans. In the discussion that follows, the term "therapeutic compounds" optionally includes a positive allosteric modulator of synaptic $GABA_A$ receptors, such as a benzodiazepine, such as midazolam, in addition to referring to an AMPA/GluR5(GluK1) kainate receptor antagonist and NMDA receptor antagonist.

The methods described herein also are suitable for use in children. Although LY293558 has been shown to be effective in adult male and female rats exposed to soman (an organophosphorus nerve agent), for example stopping seizures, protecting against neuronal damage, and preventing the development of behavioral alterations when administered 1 hour after exposure, it may not have the same effect in children. This is because, in the immature brain (such as in children) there is a high level of NMDA receptor activity, which, coupled with an augmented glutamatergic tonus due to the OP-induced AChE inhibition, leads to an increased $Ca^{2+}$ influx through the NMDA channels. This is a primary mechanism for excitotoxicity or modifications and disfigurations of the developing neuronal circuits. Moreover, the pediatric cholinergic system—which plays a central role in the mechanisms of nerve agent action—is still at a developing stage in early postnatal life. Some of the differences between immature and adult animals results in lower AChE activity in the prelimbic cortex, piriform cortex, and hippocampus of the immature animals, but not in the basolateral amygdala (BLA), which plays a key role in seizure initiation after nerve agent exposure. In addition, differences in the blood-brain barrier permeability between developing and adult animals (e.g. humans) can affect the pharmacokinetics of injected drugs used to treat nerve agent exposure. Furthermore, developing animals differ from adult animals both in seizure susceptibility and in the extent and nature of neuropathology that seizures can induce. Two particularly well-documented differences between the developing brain (such as in children) and the adult brain: (1) In the developing brain, the GABAergic inhibitory system is still weak, and its activation may produce depolarization and excitation instead of inhibition. Therefore, facilitating the GABAergic system to prevent or halt seizures in the immature brain is unlikely to produce the desired results. (2) There is high NMDA receptor activity in the immature brain, and it is well-known that Ca2+ influx through the NMDA channels is a primary mechanism for excitotoxic death, or modifications and disfigurations of the developing neuronal circuits.

The methods described herein address this by treating subjects with an NMDA receptor antagonist in addition to an AMPA/GluR5(GluK1) kainate receptor antagonist. While not wanting to be bound by theory, it is believed that the NMDA receptor antagonist may protect the immature brain from seizure-induced damage. Thus, in the context of treating children, the disclosed methods take into consideration the underdeveloped GABAergic system in the young brain and the higher activity of NMDA receptors therein. As such, the methods described herein are suitable and effective for use in adults and children. This contribution of the invention is particularly important in the context of treating subjects exposed to or at risk of exposure to nerve agents, because immature animals (such as children) have a high propensity for seizures and are very susceptible to lethality after nerve agent exposure.

As discussed in more detail below, Examples 1-11, 16-19, and 25 disclose results indicating that LY293558 either alone or in combination with caramiphen and/or midazolam is capable of treating, reducing the risks of, or preventing seizures and other effects caused by exposure to nerve agents. The disclosed combination of therapeutic compounds allows for a synergistic means of treating exposure to nerve agents and reducing the risks of or preventing the toxic effects of such agents, given the unique mechanism of action of these compounds. Additionally, combining all three disclosed types of therapeutic compounds will allow for a significant reduction in the dose of the individual compounds compared to when the compounds are administered alone.

As noted above, the disclosed methods using the disclosed combination of therapeutic compounds, also are useful for treating adults and children with neurological conditions including epilepsy, various types of seizures (e.g., refractory seizures or seizures caused by chemical (e.g. alcohol or opiate) withdrawal), PTSD, SE, depression, and anxiety.

For example, epilepsy can arise from imbalances between excitatory and inhibitory synaptic transmission in key brain areas such as the hippocampus and temporal cortex, in which fast synaptic excitatory neurotransmission is mediated via activation of ionotropic glutamate receptor. Ionotropic glutamate receptor are divided on a molecular level into NMDA receptors, AMPA receptors, and kainate receptors. As noted above, kainate receptors area further divided into multiple subtypes, and the GluR5 (GluK1) subtype is involved in the pathogenesis of epilepsy. Indeed, antagonizing GluR5 (GluK1) has been shown to inhibit pilocarpine-induced and electrically evoked epileptiform activity, such as seizures, in vitro and in vivo. NMDA receptor anatagonists are also effective in antagonizing epileptiform activity.

The disclosed combination of an AMPA/GluR5 kainate receptor antagonist (such as LY293558) and NMDA receptor antagonist (such as caramiphen), optionally in further combination with midazolam (or another benzodiazepine or positive allosteric modulator of synaptic $GABA_A$ receptors), is unexpectedly efficacious in treating, reducing the risks of, or prevent epileptic activity, such as seizures—including complex partial seizures and refractory seizures.

As discussed in more detail below, Examples 12 and 15 disclose results indicating that LY293558 alone is capable of treating, reducing the risks of, or preventing multiple types of seizures. The addition of an NMDA receptor antagonist and a positive allosteric modulator of synaptic $GABA_A$ receptors would be expected to allow for greater control and suppression of seizures, given the unique mechanism of action of these compounds. Additionally, combining all three disclosed types of therapeutic compounds will allow for a significant reduction in the dose of the individual compounds compared to when the compounds are administered alone.

With regard to anxiety and depressive disorders, the amygdala, a temporal lobe structure that is part of the limbic system, has long been recognized for its central role in emotions and emotional behavior. Pathophysiological alterations in neuronal excitability in the amygdala are characteristic features of certain psychiatric illnesses, such as anxiety disorders and depressive disorders. Furthermore, neuronal excitability in the amygdala, and, in particular, excitability of the basolateral nucleus of the amygdala (BLA) plays a pivotal role in the pathogenesis and symptomatology of temporal lobe epilepsy.

Thus, hyperexcitability of the amygdala is a characteristic of depression, anxiety disorders, and Posttraumatic Stress Disorder (PTSD). Hyperexcitability of the BLA is particularly noteworthy in these conditions, and the remarkably high expression of GluK1 kainate receptors (GluK1KRs) in the BLA may therefore serve as a target for treatment. We have investigated the role of the GluK1KRs on the modulation of GABAergic and glutamatergic transmission in the BLA, and have found that the net effect of GluK1KR activation is to increase excitability. Accordingly, blockade of GluK1KRs in the BLA has anxiolytic effects, can therefore treat depression, anxiety, or PTSD.

Indeed, LY293558, as a GluK1KR/AMPA receptor antagonist, may produce anxiolytic effects in subjects with depression, anxiety, or PTSD. Moreover, caramiphen, blocks NMDA receptors and facilitates GABAergic inhibitory transmission and depressive patients are known to respond to NMDA receptor antagonists. Evidence in rats suggests that caramiphen, in particular, has antidepressant effects. Therefore, the disclosed combination of an AMPA/GluR5 receptor antagonist (such as LY293558) and NMDA receptor antagonist (such as caramiphen), optionally in further combination with midazolam (or another benzodiazepine or other positive allosteric modulator of synaptic $GABA_A$ receptors), may have superior antidepressant and anxiolytic effects than the current standard of care treatments.

Epilepsy and epileptic seizures that similarly have been shown to be associated with neuronal excitability in the BLA, and the relevance of the GluR5KR function to epilepsy is suggested by the findings that GluR5KR agonists can induce epileptic activity, whereas GluR5KR antagonists can prevent it. Further support for an important role of GluR5KRs in epilepsy comes from the findings that antagonism of GluR5KRs is a primary mechanism underlying the antiepileptic properties of the anticonvulsant topiramate.

The disclosed combination of therapeutic compounds may also be useful for treating, reducing the risks of, or preventing seizures caused by withdrawal from chemicals (e.g., alcohol or illicit drugs or opiates). Additionally, the disclosed combination of therapeutic compounds may be useful for treating Neonatal Abstinence Syndrome (NAS) or reducing the risks of or preventing the long term psychological and physiological effects of NAS. Indeed, antagonism of both AMPA and GluR5 receptors has been shown to attenuate morphine-withdrawal-induced activation of locus coeruleus neurons and behavioral signs of morphine withdrawal. In an animal model of morphine withdrawal, pretreatment with LY293558 significantly reduced the signs of morphine withdrawal in awake animals, including significant decreases in the occurrence of writhes, wet-dog shakes, stereotyped head movements, ptosis, lacrimation, salivation, diarrhea, and chews. We expect that adding an NMDA receptor antagonist to the treatment will improve the attenuation of withdrawal symptoms, including withdrawal-induced seizures, by modulating an alternative pathway that has also been implicated withdrawal-induced behavior and symptoms.

As discussed in more detail below, Examples 13, 14, 23, and 24 disclose results indicating that LY293558 alone is capable of treating symptoms of withdrawal (such as seizures) from alcohol, opiates and other chemicals. The addition of an NMDA receptor antagonist and a positive allosteric modulator of synaptic $GABA_A$ receptors would be expected to allow for greater control and suppression of withdrawal-induced seizures and other symptoms, given the unique mechanism of action of these compounds. Additionally, combining all three disclosed types of therapeutic compounds will allow for a significant reduction in the dose of the individual compounds compared to when the compounds are administered alone.

The present disclosure provides novel mechanisms for regulating neuronal excitability in the BLA by modulating GABAergic inhibitory transmission using the disclosed combination of therapeutic compounds. These mechanisms involve the regulation of GABA release via both presynaptic and postsynaptic kainate receptors containing the GluR5 (GluK1) subunit, by administering an AMPA/GluR5 kainate receptor antagonist (such as LY293558), and via NMDA receptors, by administering an NMDA receptor antagonist (such as caramiphen), optionally in further combination with midazolam (or another benzodiazepine or another positive allosteric modulator of synaptic $GABA_A$ receptors). This is particularly important not only in seizures and epilepsy, but also in anxiety disorders and depression, which have been found to be associated with decreased GABA activity in the BLA due to downregulation of $\alpha_{1A}$ adrenergic receptors.

Pharmaceutical Compositions

The therapeutic compounds may be provided in the same or different pharmaceutical compositions, which may include one or both of the therapeutic compounds and a pharmaceutically acceptable carrier or diluent. In embodiments where a positive allosteric modulator of synaptic $GABA_A$ receptors, such as a benzodiazepine, such as midazolam, also is being used, it may be provided in the same composition as one or both of the other therapeutic compounds, or in a different pharmaceutical composition.

The pharmaceutical compositions may be formulated for any route of administration, such as intravenous, subcutaneous, intraperitoneal, intramuscular, oral, nasal, pulmonary, ocular, vaginal, or rectal administration. In some embodiments, one or both of the therapeutic compounds are formulated for injection or infusion, such as being formulated in a solution, suspension, emulsion, liposome formulation, etc. In some embodiments, one or both of the therapeutic compounds are formulated for oral administration, such as in a tablet, capsule, powder, granule, or liquid form suitable for oral administration. The pharmaceutical compositions can be formulated to be immediate-release compositions, sustained-release compositions, delayed-release compositions, and combinations thereof, etc., using techniques known in the art. In some embodiments, the therapeutic compounds are formulated for injection, such as intramuscular injection, and administered by injection as a first treatment of exposure to a nerve agent. In some embodiments, the therapeutic compounds are formulated for oral administration and administered orally to provide a subsequent treatment, such as for maintenance therapy.

Suitable pharmacologically acceptable carriers and diluents for various dosage forms are known in the art. For example, excipients, lubricants, binders, and disintegrants for solid preparations are known; solvents, solubilizing agents, suspending agents, isotonicity agents, buffers, and soothing agents for liquid preparations are known. In some embodiments, the pharmaceutical compositions include one or more additional components, such as one or more preservatives, antioxidants, colorants, sweetening/flavoring agents, adsorbing agents, wetting agents and the like.

Methods of Treatment

As noted above, the methods disclosed herein are effective for treating or reducing the toxic effects of exposure to a nerve agent, comprising administering to a subject in need thereof (i) an AMPA/GluR5(GluK1) kainate receptor antagonist and (ii) an NMDA receptor antagonist, as described above. In another aspect, the present disclosure provides methods for treating, reducing the risks of, or preventing the effects of neurological conditions, such as epilepsy, seizures (e.g., refractory seizures, seizures caused by chemical (e.g. alcohol or opiate) withdrawal), post-traumatic stress disorder (PTSD), status epilepticus (SE), depression, or anxiety, comprising administering to a subject in need thereof (i) an AMPA/GluR5(GluK1) kainate receptor antagonist and (ii) an NMDA receptor antagonist, as described above. In any embodiments, the methods may further comprise administering a therapeutically effective amount of a positive allosteric modulator of synaptic $GABA_A$ receptors, such as a benzodiazepine, such as midazolam.

As noted above, the therapeutic compounds may be provided in a single composition or in separate compositions, and may be administered substantially simultaneously or sequentially with the compounds administered in any order. For example, the AMPA/GluR5(GluK1) kainate receptor antagonist may be administered prior to the administration of the NMDA receptor antagonist, or the AMPA/GluR5(GluK1) kainate receptor antagonist may be administered after to the administration of the NMDA receptor antagonist. Further, the positive allosteric modulator of synaptic $GABA_A$ receptors (e.g., a benzodiazepine such as midazolam) may be administered prior to the AMPA/GluR5(GluK1) kainate receptor antagonist and the NMDA receptor antagonist, after the AMPA/GluR5(GluK1) kainate receptor antagonist and the NMDA receptor antagonist, or between the AMPA/GluR5(GluK1) kainate receptor antagonist and the NMDA receptor antagonist, with either the AMPA/GluR5(GluK1) kainate receptor antagonist or the NMDA receptor antagonist being administered first. As used herein "substantially simultaneously" means that the compounds are administered at the same time or within up to about 1 minute, about 2 minutes, about 3, about 4, about 5, about 6, about 7, about 8, about 9, about 10, about 11, about 12, about 13, about 14, about 15, about 16, about 17, about 18, about 19, or about 20 minutes of one another.

As noted above, the therapeutic compounds may be administered by any suitable route of administration, such as intravenously, subcutaneously, intraperitoneally, intramuscularly, orally, nasally, buccally, pulmonarily, ocularly, vaginally, or rectally. In some embodiments, the therapeutic compounds are administered via injection, such as intramuscular injection. When the therapeutic compounds are administered separately, they may be administered via the same route of administration or different routes of administration. For example, the AMPA/GluR5(GluK1) kainate receptor antagonist may be administered via injection (e.g. intramuscular injection) and the NMDA receptor antagonist may be administered orally, or vice versa. The positive allosteric modulator of synaptic $GABA_A$ receptors (e.g., a benzodiazepine such as midazolam) may be administered orally, buccally, nasally, intravenously, or intramuscularly, and it may be administered via the same route as either one or both of the AMPA/GluR5(GluK1) kainate receptor antagonist and the NMDA receptor antagonist, or may be administered via a different route than the AMPA/GluR5(GluK1) kainate receptor antagonist and the NMDA receptor antagonist.

The methods may be used to treat or reduce the toxic effects of exposure to one or more nerve agents, including organophosphorus nerve agents and other chemicals that inhibit the activity of acetylcholinesterase. Exemplary, non-limiting examples of such nerve agents include sarin, soman, tabun, and cyclosarin. The methods may be used to treat, reduce the risks of or prevent the effects of neurological conditions comprising epilepsy, seizures (e.g., refractory seizures, seizures caused by chemical (e.g. alcohol or opiate) withdrawal), PTSD, SE, depression, or anxiety One particular clinical benefit of the disclosed methods as compared to prior methods of treating exposure to nerve agents (i.e., administration of diazepam) is that the methods described herein can be effective even when the therapeutic compounds are administered at a later time post-exposure. For example, in accordance with the methods described herein, as subject may first be treated within up to 5 minutes, 10 minutes, 20 minutes, 30 minutes, 45 minutes, 60 minutes, 75 minutes, 90 minutes or up to 120 minutes after exposure. For example, in some embodiments, a subject is administered an AMPA/GluR5(GluK1) kainate receptor antagonist and NMDA receptor antagonist within 20 minutes or less after exposure to the nerve agent, within one hour or less after exposure to the nerve, or within two hours or less after exposure to the nerve agent.

As discussed above, the disclosed methods can be used to treat a range of subjects, including human and non-human animals, including mammals, as well as immature and mature animals, including human children and adults. In some embodiments, the subject has been exposed to a nerve agent, in other embodiments, the subject is suspected of having been exposed to a nerve agent, while in other embodiments the subject is at risk of exposure to a nerve agent. In some embodiments, the subject has been diagnosed as having one or more neurological conditions, such as one or more of epilepsy, seizures (e.g., refractory seizures, seizures caused by chemical or opiate withdrawal), PTSD, SE, depression, or anxiety. In other embodiments, the subject is suspected of having one or more neurological conditions, while in other embodiments, the subject is at risk of developing one or more of neurological conditions.

As discussed above, the disclosed methods are effective to treat or reduce the risks of physiological consequences or toxic effects of exposure to the nerve agent including, but not limited to, seizures, status epilepticus, brain damage, neurological effects, behavioral effects, difficulty breathing, nausea, loss of control of bodily functions, and death. Likewise, the disclosed methods can treat epilepsy, various types of seizures, PTSD, SE, depression, or anxiety, or decrease the symptoms or effects of any of these conditions.

In some embodiments, the method comprises administering a single dose of the therapeutic compounds (e.g., LY293558 and CRM), and, optionally, a single dose of the positive allosteric modulator of synaptic $GABA_A$ receptors (e.g., a benzodiazepine such as midazolam). In some embodiments administering a single dose of the therapeutic compounds is effective to treat the exposure, i.e., to treat, reduce, ameliorate, or eliminate one or more of the physiological consequences of exposure, or to treat the neurological condition of the subject. In some embodiments, the method comprises administering repeated doses of one or more of the therapeutic compounds, such as repeated doses of LY293558 and CRM, and/or repeated doses of midazolam, such as may be needed for one or more symptoms or effects to be treated, reduced, ameliorated, or eliminated.

For instance, an individual that has been exposed to a nerve agent may be evaluated for the presence and/or severity of signs and symptoms associated with nerve agent intoxication, including, but not limited to, seizures, status epilepticus, brain damage, neurological effects, behavioral effects, difficulty breathing, nausea, or loss of control of bodily functions, and may be treated with one or more of the therapeutic compounds described herein until one or more of the signs/symptoms is reduced, ameliorated, or eliminated with treatment. Similarly, a subject with epilepsy, seizures, PTSD, depression, or anxiety may be evaluated for the presence and/or severity of signs and symptoms associated with these conditions and may be treated with one or more of the therapeutic compounds as described herein until one or more of the signs/symptoms is reduced, ameliorated, or eliminated. In some embodiments, treatment is repeated with additional doses of one or more of the therapeutic compounds if signs/symptoms/effects persist and can be continued (or repeated) until one or more symptoms or effects of nerve agent intoxication are reduced, ameliorated, or eliminated.

In some embodiments, the method comprises administering periodic doses of one or more of the therapeutic compounds, such as may be needed to maintain recovery status after an initial treatment. That is, not only are the disclosed methods effective for treating or reducing the risk of acute or recent exposure to a nerve agent, the disclosed methods also can be effective as maintenance therapy to maintain recovery status and/or improve long-term outcome of subjects who have been exposed to a nerve agent, or of subjects suffering from a neurological disorder. Maintenance therapy may comprise at least one, at least two, at least three, at least four, at least five, at least six, at least seven, at least eight, at least nine, or at least ten subsequent administrations of the therapeutic compounds (AMPA/GluR5(GluK1) kainate receptor antagonist and NMDA receptor antagonist) and, optionally, the positive modulatory of synaptic GABA-A receptors (e.g., a benzodiazepine such as midazolam). For the purposes of treating the neurological conditions disclosed herein, chronic maintenance therapy may be useful for treating, reducing the risks of, or preventing, for example, epileptic seizures, depression, anxiety, or PTSD, while treating seizures arising from chemical (e.g. alcohol or opiate) withdrawal may only require treatment for a limited period of time after detoxification has begun.

We have found that the lowest effective dose (LED) of LY293558, administered alone (i.m.), is 15 mg/kg, and that of caramiphen is 100 mg/kg (i.m.). These doses are close to the median toxic doses ($TD_{50}$) for LY293558 (20 mg/kg) and caramiphen (162 mg/kg), respectively. Thus, the disclosed combination therapy would be very beneficial as a treatment because it would allow the doses of LY293558 and caramiphen to be reduced considerably, thus decreasing the incidence of side effects and increasing the tolerability of the disclosed treatment in humans. This is because LY293558 and caramiphen produce their respective pharmacological effect via different mechanisms of action, which fosters a synergistic effect for the disclosed methods of treatment. Based on the pilot studies disclosed in the Examples, an effective dose of LY293558 used in combination with caramiphen could be from about 2 to about 5 mg/kg (i.m.), and an effective dose of caramiphen used in combination with LY293558 could be from about 10 to about 20 mg/kg (i.m.). As noted above, doses could be further reduced with a triple therapy approach.

Thus, in the methods described herein, the dose of LY293558 may be from about 2 to about 20 mg/kg (i.m.), from about 2 to about 15 mg/kg (i.m.), or from about 2 to about 5 mg/kg (i.m.) when used in combination with caramiphen, or less when used in combination with caramiphen and midazolam. Thus, the dose of LY293558 may be about 0.025, about 0.05, about 0.075, about 0.1, about 0.25, about 0.5, about 0.75, about 1.0, about 0.25, about 0.5, about 0.75, about 1.0, about 1.25, about 1.5, about 1.75, about 2.0, about 2.25, about 2.5, about 2.75, about 3.0, about 3.25, about 3.5, about 3.75, about 4.0, about 4.25, about 4.5, about 4.75, about 5.0, about 5.25, about 5.5, about 5.75, about 6.0, about 6.25, about 6.5, about 6.75, about 7.0, about 7.25, about 7.5, about 7.75, about 8.0, about 8.25, about 8.5, about 8.75, about 9.0, about 9.25, about 9.5, about 9.75, about 10.0, about 10.25, about 10.5, about 10.75, about 11.0, about 11.25, about 11.5, about 11.75, about 12.0, about 12.25, about 12.5, about 12.75, about 13.0, about 13.25, about 13.5, about 13.75, about 14.0, about 14.25, about 14.5, about 14.75, about 15.0, about 15.25, about 15.5, about 15.75, about 16.0, about 16.25, about 16.5, about 16.75, about 17.0, about 17.25, about 17.5, about 17.75, about 18.0, about 18.25, about 18.5, about 18.75, about 19.0, about 19.25, about 19.5, about 19.75, about 20.0, about 21.0, about 21.25, about 21.5, about 21.75, about 22.0, about 22.25, about 22.5, about 22.75, about 23.0, about 23.25, about 23.5, about 23.75, about 24.0, about 24.25, about 24.5, about 24.75, about 25.0 or greater mg/kg (i.m.), or equivalent doses for a different route of administration.

In the methods described herein, the dose of caramiphen may be from about 10 to about 162 mg/kg (i.m.), or from about 10 to about 100 mg/kg (i.m.), or from about 10 to about 20 mg/kg (i.m.) when used in combination with LY293558, or less when used in combination with LY293558 and midazolam. Thus, the dose of caramiphen may be about 1.0, about 0.25, about 0.5, about 0.75, about 1.0, about 1.25, about 1.5, about 1.75, about 2.0, about 2.25, about 2.5, about 2.75, about 3.0, about 3.25, about 3.5, about 3.75, about 4.0, about 4.25, about 4.5, about 4.75, about 5.0, about 5.25, about 5.5, about 5.75, about 6.0, about 6.25, about 6.5, about 6.75, about 7.0, about 7.25, about 7.5, about 7.75, about 8.0, about 8.25, about 8.5, about 8.75, about 9.0, about 9.25, about 9.5, about 9.75, about 10.0, about 10.25, about 10.5, about 10.75, about 11.0, about 11.25, about 11.5, about 11.75, about 12.0, about 12.25, about 12.5, about 12.75, about 13.0, about 13.25, about 13.5, about 13.75, about 14.0, about 14.25, about 14.5, about 14.75, about 15.0, about 15.25, about 15.5, about 15.75, about 16.0, about 16.25, about 16.5, about 16.75, about 17.0, about 17.25, about 17.5, about 17.75, about 18.0, about 18.25, about 18.5, about 18.75, about 19.0, about 19.25, about 19.5, about 19.75, about 20.0, about 20.25, about 20.5, about 20.75, about 21.0, about 21.25, about 21.5, about 21.75, about 22.0, about 22.25, about 22.5, about 22.75, about 23.0, about 23.25, about 23.5, about 23.75, about 24.0, about 24.25, about 24.5, about 24.75, about 25.0, about 25.25, about 25.5, about 25.75, about 26.0, about 26.25, about 26.5, about 26.75, about 27.0, about 27.25, about 27.5, about 27.75, about 28.0, about 28.25, about 28.5, about 28.75, about 29.0, about 29.25, about 29.5, about 29.75, about 30.0, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 100, about 101, about 102, about 103, about 104, about 105, about 106, about 107, about 108, about 109. About 110, about 111, about 112, about 113, about 114, about 115, about 116, about 117, about 118, about 119, about 120, about 121, about 122, about 123, about 124, about 125, about 126, about 127, about 128, about 129, about 130, about 131, about 132, about 133, about 134, about 135, about 136, about 137, about 138, about 139, about 140, about 141, about 142, about 143, about 144, about 145, about 146, about 147, about 148, about 149, about 150, about 151, about 152, about 153, about 154, about 155, about 156, about 157, about 158, about 159, about 160, about 161, about 162 or greater mg/kg (i.m.), or equivalent doses for a different route of administration.

In the methods described herein, the dose of midazolam may be from about 2 to about 10 mg/kg (i.m.). Thus, the dose of midazolam may be about 2.0, about 2.25, about 2.5, about 2.75, about 3.0, about 3.25, about 3.5, about 3.75, about 4.0, about 4.25, about 4.5, about 4.75, about 5.0, about 5.25, about 5.5, about 5.75, about 6.0, about 6.25, about 6.5, about 6.75, about 7.0, about 7.25, about 7.5, about 7.75, about 8.0, about 8.25, about 8.5, about 8.75, about 9.0, about 9.25, about 9.5, about 9.75, about 10.0, or equivalent doses for a different route of administration.

As noted above, whenever multiple doses of the therapeutic compounds are administered, they may be administered in the same or different compositions and by the same or different routes of administration as a previous dose. For instance, in some embodiments, the initial administration of the therapeutic compounds may be by intramuscular injection and a subsequent administration be by oral administration. Alternatively, all administrations may be by intramuscular injection or all administrations may be orally. Or each therapeutic compound may be administered by a different route.

EMBODIMENTS

The following is a list of non-limiting exemplary embodiments.

1. A method of treating or reducing the toxic effects of exposure to a nerve agent, comprising administering to a subject in need thereof (i) an AMPA/GluR5(GluK1) kainate receptor antagonist and (ii) an NMDA receptor antagonist.

2. A method of treating, reducing the risks of, or preventing a neurological condition, comprising administering to a subject in need thereof (i) an AMPA/GluR5(GluK1) kainate receptor antagonist and (ii) an NMDA receptor antagonist.

3. The method of embodiment 2, wherein the neurological condition is epilepsy, seizure, post-traumatic stress disorder, status epilepticus, depression, or anxiety.

4. The method of any one of embodiments 1-3, wherein the AMPA/GluR5(GluK1) kainate receptor antagonist is LY293558.

5. The method of any one of embodiments 1-4, wherein the NMDA receptor antagonist is an antimuscarinic compound.

6. The method of any one of embodiments 1-5, wherein the NMDA receptor antagonist is caramiphen.

7. The method of any one of embodiments 1-6, further comprising administering a positive allosteric modulator of synaptic $GABA_A$ receptors to the subject.

8. The method of embodiment 7, wherein the positive allosteric modulator of synaptic $GABA_A$ receptors is a benzodiazepine.

9. The method of embodiment 7, wherein the positive allosteric modulator of synaptic $GABA_A$ receptors is midazolam.

10. The method of any one of embodiments 1-9, wherein the AMPA/GluR5(GluK1) kainate receptor antagonist and the NMDA receptor antagonist, and, optionally, the positive allosteric modulator of synaptic $GABA_A$ receptors, are administered in the same composition.

11. The method of any one of embodiments 1-9, wherein the AMPA/GluR5(GluK1) kainate receptor antagonist and the NMDA receptor antagonist, and, optionally, the positive allosteric modulator of synaptic $GABA_A$ receptors, are administered in separate compositions, by the same route of administration or by different routes of administration.

12. The method of embodiment 11, wherein the AMPA/GluR5(GluK1) kainate receptor antagonist and the NMDA receptor antagonist, and, optionally, the positive allosteric modulator of synaptic $GABA_A$ receptors, are administered substantially simultaneously.

13. The method of embodiment 11, wherein the AMPA/GluR5(GluK1) kainate receptor antagonist and the NMDA receptor antagonist, and, optionally, the positive allosteric modulator of synaptic $GABA_A$ receptors, are administered sequentially.

14. The method of embodiment 13, wherein the AMPA/GluR5(GluK1) kainate receptor antagonist is administered prior to the administration of the NMDA receptor antagonist.

15. The method of embodiment 13, wherein the AMPA/GluR5(GluK1) kainate receptor antagonist is administered after to the administration of the NMDA receptor antagonist.

16. The method of embodiment 13, wherein the positive allosteric modulator of synaptic $GABA_A$ receptors is administered prior to both the AMPA/GluR5(GluK1) kainate receptor antagonist and the NMDA receptor antagonist, after both the AMPA/GluR5(GluK1) kainate receptor antagonist and the NMDA receptor antagonist, or prior to one of the AMPA/GluR5(GluK1) kainate receptor antagonist and the NMDA receptor antagonist and after the other of the AMPA/GluR5(GluK1) kainate receptor antagonist and the NMDA receptor antagonist.

17. The method of any one of embodiments 1-16, wherein the AMPA/GluR5(GluK1) kainate receptor antagonist and the NMDA receptor antagonist and, optionally, the positive allosteric modulator of synaptic $GABA_A$ receptors, are administered by injection.

18. The method of embodiment 17, wherein the injection is an intramuscular injection.

19. The method of any one of embodiments 1-16, wherein the AMPA/GluR5(GluK1) kainate receptor antagonist and the NMDA receptor antagonist and, optionally, the positive modulator of synaptic GABA-A receptors, are administered orally.

20. The method of any one of embodiments 1 and 4-19, wherein the nerve agent comprises an organophosphorus toxin.

21. The method of any one of embodiments 1 and 4-19, wherein the nerve agent comprises soman.

22. The method of any one of embodiments 1 and 4-19, wherein the nerve agent comprises sarin.

23. The method of any one of embodiments 1 and 4-19, wherein the subject has been exposed to a nerve agent.

24. The method of embodiment 23, wherein administration of the AMPA/GluR5(GluK1) kainate receptor antagonist and NMDA receptor antagonist occurs within 20 minutes or less of exposure to the nerve agent.

25. The method of embodiment 23, wherein administration of the AMPA/GluR5(GluK1) kainate receptor antagonist and NMDA receptor antagonist occurs within one hour or less of exposure to the nerve agent.

26. The method of embodiment 23, wherein administration of the AMPA/GluR5(GluK1) kainate receptor antagonist and NMDA receptor antagonist occurs within two hours or less of exposure to the nerve agent.

27. The method of any one of embodiments 1 and 4-19, wherein the subject is suspected of having been exposed to a nerve agent.

28. The method of any one of embodiments 1 and 4-19, wherein the subject is at risk of exposure to a nerve agent.

29. The method of any one of embodiments 1 and 4-28, wherein the method is effective to treat or reduce the toxic effects of exposure to the nerve agent selected from one or more of seizures, status epilepticus, brain damage, neurological effects, behavioral effects, difficulty breathing, nausea, loss of control of bodily functions, and death.

30. The method of any one of embodiments 3-19, wherein the seizure is a refractory seizure, an epileptic seizure, or a seizure induced by withdrawal from a chemical (e.g. alcohol or opiate).

31. The method of embodiment 30, wherein the seizure is a seizure induced by withdrawal from a chemical.

32. The method of embodiment 31, wherein administration of the AMPA/GluR5(GluK1) kainate receptor antagonist and NMDA receptor antagonist and, optionally, the positive allosteric modulator of synaptic $GABA_A$ receptors, occurs prior to withdrawal of the chemical.

33. The method of embodiment 31, wherein administration of the AMPA/GluR5(GluK1) kainate receptor antagonist and NMDA receptor antagonist, and, optionally, the positive allosteric modulator of synaptic $GABA_A$ receptors, occurs during detoxification of the subject.

34. The method of embodiment 31, wherein administration of the AMPA/GluR5(GluK1) kainate receptor antagonist and NMDA receptor antagonist, and, optionally, the positive allosteric modulator of synaptic $GABA_A$ receptors, occurs after withdrawal of the chemical.

35. The method of any one of embodiments 2-19, wherein the subject has been diagnosed with the neurological condition.

36. The method of any one of embodiments 2-19, wherein the method is effective to treat or reduce signs or symptoms of the neurological condition.

37. The method of any one of the preceding embodiments, further comprising at least one subsequent administration of the AMPA/GluR5(GluK1) kainate receptor antagonist and NMDA receptor antagonist and, optionally, the positive allosteric modulator of synaptic $GABA_A$ receptors, as maintenance therapy.

38. The method of embodiment 37, wherein the at least one subsequent administration is administered by injection.

39. The method of embodiment 37, wherein the at least one subsequent administration is administered orally.

40. The method of any one of the preceding embodiments, wherein the subject is a mammal.

41. The method of any one of the preceding embodiments, wherein the subject is a human child.

42. The method of any one of the preceding embodiments, wherein the subject is a human adult.

43. An AMPA/GluR5(GluK1) kainate receptor antagonist and an NMDA receptor antagonist, and, optionally a positive allosteric modulator of synaptic $GABA_A$, as described herein, for treating or reducing the toxic effects of exposure to a nerve agent, as described herein.

44. An AMPA/GluR5(GluK1) kainate receptor antagonist and an NMDA receptor antagonist, and, optionally a positive allosteric modulator of synaptic $GABA_A$, as described herein, for treating or reducing the risks of a neurological condition, as described herein.

45. Use of an AMPA/GluR5(GluK1) kainate receptor antagonist and an NMDA receptor antagonist, and, optionally a positive allosteric modulator of synaptic $GABA_A$, as described herein, in the preparation of one or more medicaments as described herein for treating or reducing the toxic effects of exposure to a nerve agent.

46. Use of an AMPA/GluR5(GluK1) kainate receptor antagonist and an NMDA receptor antagonist, and, optionally a positive allosteric modulator of synaptic $GABA_A$, as described herein, in the preparation of one or more medicaments as described herein for treating or reducing the risks of a neurological condition as described herein.

The following examples are given to illustrate the present invention. It should be understood, however, that the invention is not to be limited to the specific conditions or details described in these examples. All printed publications referenced herein are specifically incorporated by reference.

EXAMPLES

In the following experiments, unless otherwise stated, male and female rats are used to detect any gender-related differences in the responses to soman and/or the treatments. 21 day-old rats (P21) are used as models of 3-4-year old human children. 12-day old rats (P12) can be used as models of a newborn human.

Example 1—Combination Treatment of Adult Soman-Exposed Rats Stops Seizures

Glutamatergic excitation is reinforced during SE, not only because of disinhibition, but also because during SE there is up-regulation of AMPA receptors, as well as enhanced expression of the GluK1 subunit, which could significantly contribute to worsening hyperexcitability and excitotoxicity. Therefore, suppressing glutamatergic hyperactivity can be a more effective way to control seizures, particularly if immediate treatment is not possible and the treatment is administered with a delay after seizure onset.

For example, LY293558 administered to adult rats 1 hour after exposure to soman stops seizures and fully protects against neuronal damage, and prevents increase in anxiety-like behavior and the associated pathophysiological alterations in the basolateral amygdala (BLA). Similar results were obtained in 21 day-old rats (P21 rats). While not wanting to be bound by theory, in addition to suppressing AMPA receptor activity, the efficacy of LY293558 may lie on the fact that GluK1Rs play an important role in the regulation of neuronal excitability of at least two highly seizure-prone regions, the amygdala and the hippocampus. Both GABAergic and glutamatergic synaptic transmission are modulated by GluK1Rs in different brain regions, but the net effect of GluK1R activation appears to be an increase in excitability in both the BLA and the hippocampus.

Caramiphen (CRM) is an M1 muscarinic receptor antagonist, but it has also been known to have antiglutamatergic properties. In the rat BLA, CRM antagonizes NMDA receptors. While not wanting to be bound by theory, this is probably because of its NMDAR antagonistic properties that CRM can terminate nerve agent induced-seizures and provide neuroprotection at latencies after exposure that are longer than those at which other muscarinic antagonists (that do not have antiglutamatergic properties) are efficacious. When administered to adult rats, CRM displayed both anti-seizure and neuroprotective effects even when administered at 30 minutes or 60 minutes after soman exposure; however, it took 1 to 2 hours for the behavioral seizure score to fall below stage 2.

Since CRM has pharmacological properties (NMDA antagonistic and antimuscarinic) that LY293558 does not have, a method using both therapeutic compounds provides additional protection, as shown in the following experiments.

Figures 22A, 22B, 22C:
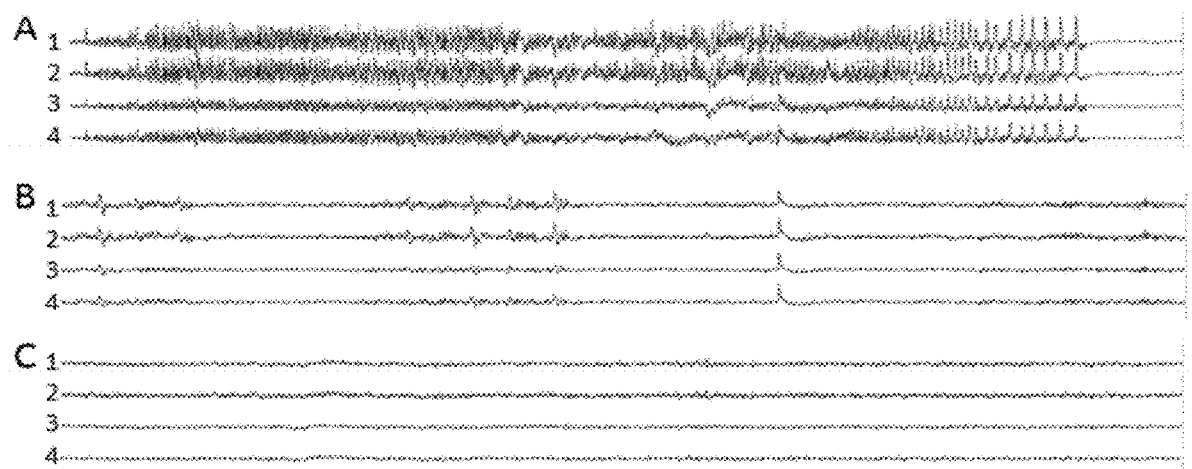
FIGS. 22A-22C show that the combination of CRM and LY293558 protects against the development of epilepsy after soman exposure ($1.2 \times LD_{50}$). Representative EEG tracings (60 s duration) 7 days after exposure to $1.2 \times LD_{50}$ of soman.
Figures 23A, 23B, 23C:
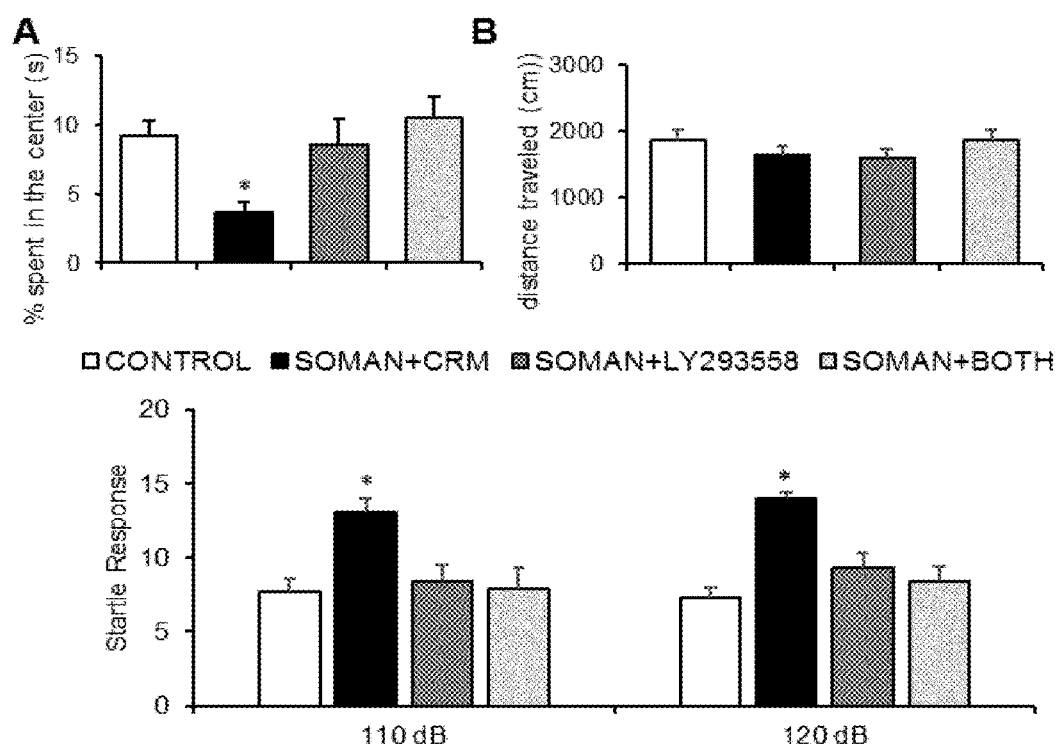
FIGS. 23A-23C show increased anxiety in the open field and acoustic startle response tests, 30 days after soman exposure, was prevented by administration of LY2935578 or combination of LY293558 and caramiphen in P12 rats.
Figures 25A, 25B, 25C:
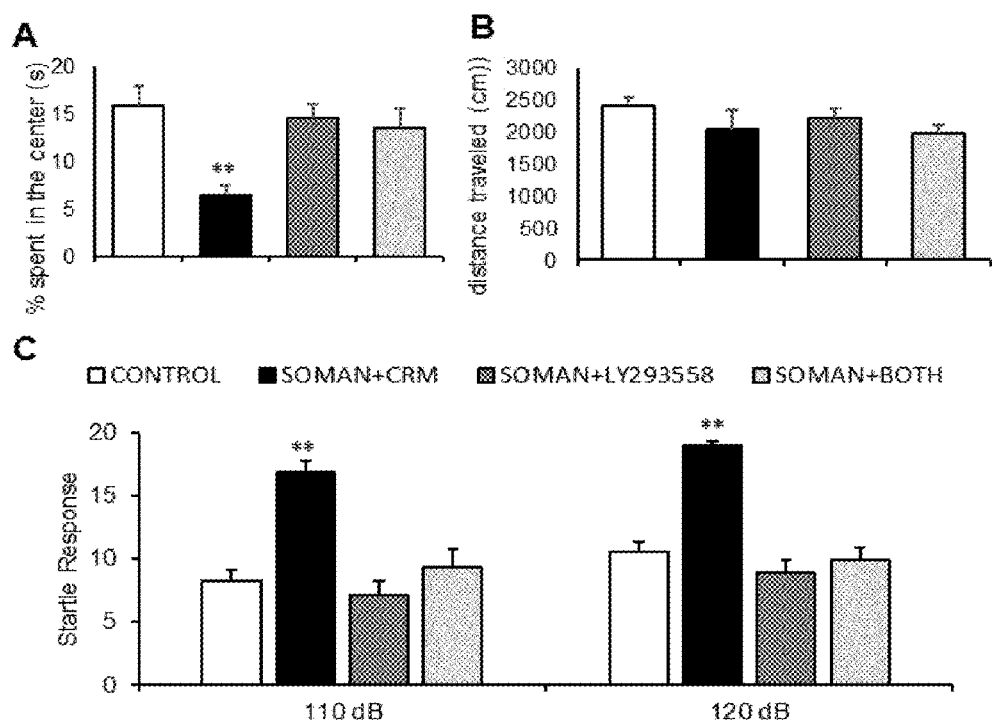
FIGS. 25A-25C show increased anxiety in the open field and acoustic startle response 3 months after soman exposure were prevented by administration of LY2935578 or combination of LY293558 and caramiphen, in P12 rats.

Adult male rats were treated with LY293558 (15 mg/kg) and/or CRM (50 mg/kg) after being exposed to 1.2×LD$_{50}$ soman (132 µg/kg; LD$_{50}$=110 µg/kg in adult rats). Electrodes were placed at various locations on the rats' brains (see FIG. 1C; 1: left frontal; 2: right frontal; 3: left parietal; 4: right parietal; un-labeled: cerebellar reference electrode) to record electrical activity and assess the duration of initial SE and the duration of SE during a 7-day period after exposure. FIG. 1A shows the time course of seizure suppression by LY293558, while FIG. 1B shows the time course of seizure suppression by LY293558+CRM, revealing a faster time-course of suppression by treatment of adult rats with LY293558+CRM. FIG. 1D shows a significantly shorter duration of both initial SE and total duration of SE during the 7 day period after exposure in the LY293558+CRM group. FIG. 1D, left panel, shows the duration of the initial SE, which is the SE that started within 6-10 min after soman exposure and was terminated by 15 mg/kg LY293558 (open bar), or 15 mg/kg LY293558 and 50 mg/kg CRM (closed bar). FIG. 1D, right panel, shows the duration of SE throughout the 7 day-period after soman exposure for the same two groups. The corresponding durations for the untreated soman group (not shown) are about 700 min for the initial SE and more than 1000 min for the 7-day-period. *p<0.05 (Unequal Variance t-test). Thus, the combination treatment reduced the duration of the initial SE and the total duration of SE as compared to treatment with LY293558 alone. Representative EEG tracings are shown in FIGS. 1A-1B, and additional, expended EEGs are shown in FIGS. 22A-22C.

Example 2—Combination Treatment of Adult Soman-Exposed Rats Prevents Neuronal Degradation To understand whether LY293558 alone or in combination with CRM was more effective at preventing soman-induced neuronal degradation, adult rats were exposed to 1.2×LD$_{50}$ soman (132 µg/kg) and then treated with LY293558 (15 mg/kg) and/or CRM (50 mg/kg) 20 minutes after soman exposure. Seven days after soman exposure, brain sections were taken and Nissl-stained and scored or stained with Fluoro-Jade C. Results are shown in FIG. 2.

Figures 2A, 2B, 2C, 2D:
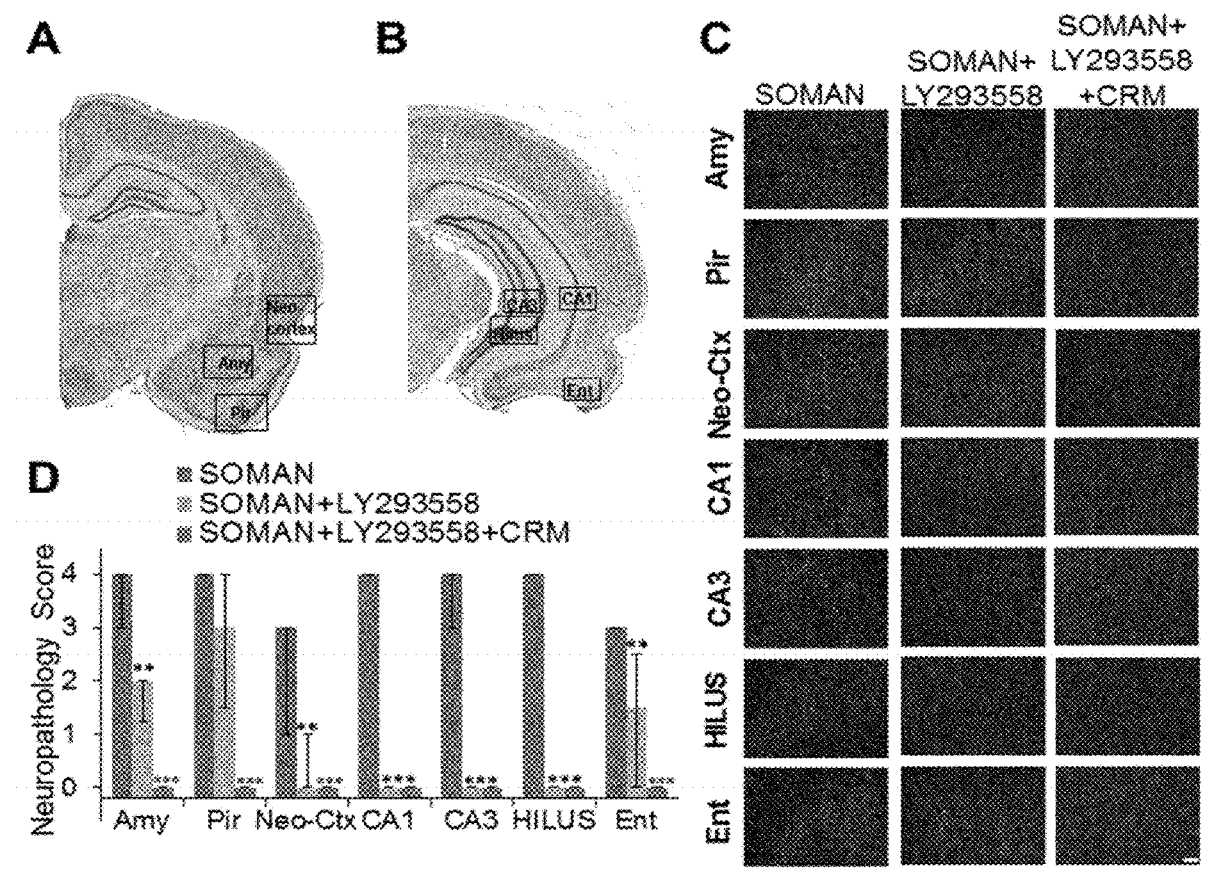
FIGS. 2A-D show that the methods described herein are superior to treatment with LY293558 alone in preventing soman-induced neuronal degeneration 7 days after exposure in a rat model.

FIGS. 2A-D show that treatment with LY293558 and CRM is superior to treatment with LY293558 alone in preventing soman-induced neuronal degeneration 7 days after exposure in adult rats. FIGS. 2A and 2B show panoramic photomicrographs of Nissl-stained sections showing the brain regions from the Fluoro-Jade C photomicrographs shown in FIG. 2C. FIG. 2C shows representative photomicrographs of Fluoro-Jade C stained sections from the brain regions where neuronal degeneration was evaluated, for the untreated (SOMAN), LY293558-treated (SOMAN+LY293558) and LY293558- and CRM-treated (SOMAN+LY293558+CRM) groups. Total magnification is 100×. Scale bar is 50 µm. FIG. 2D shows median neuropathology score and interquartile range for the amygdala (Amy), piriform cortex (Pir), entorhinal cortex (Ent), the CA1 and CA3 subfields of the ventral hippocampus, hilus, and neocortex (neo-Ctx).

Overall, this study shows that treatment with LY293558 and CRM is effective at preventing neurodegeneration in all brain regions following soman exposure.

Figure 3:
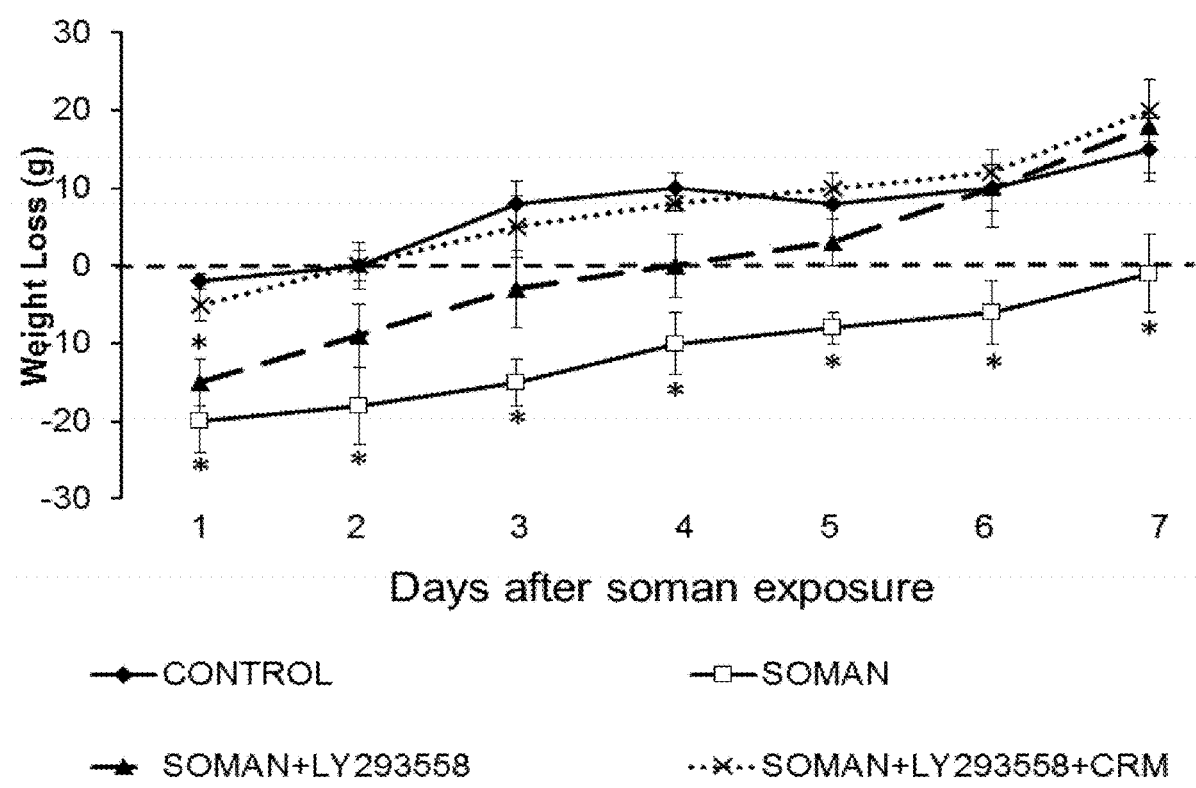
FIG. 3 shows results of weight loss study during 7 days after soman exposure in a rat model. Soman-exposed rats that did not receive anticonvulsant treatment (n=18) display dramatic weight loss and reduced weight gain. Rats treated with LY293558 only (n=18) exhibited significantly improved weight-gain response, while rats treated with LY293558+CRM (n=19) do not display any difference from control rats (n=18) that were not exposed to soman.

Example 3—Combination Treatment of Adult Soman-Exposed Rats Prevents Weight Loss Adult rats were treated as outlined in Examples 1 and 2 and weighed every day for seven days. Results are shown in FIG. 3. Soman-exposed rats that did not receive treatment (Soman, n=18) displayed dramatic weight loss and reduced weight gain. Soman-exposed rats treated with LY293558 only (n=18) exhibited significantly improved weight-gain response compared to the rats that did not receive the drug, while soman-exposed rats treated with both LY293558 and CRM (n=19) did not display any difference from control rats (n=18) that were not exposed to soman. Overall, this study shows that the combination of LY293558 and CRM is effective at preventing weight loss following soman exposure.

Collectively, the results of Examples 1-3 indicate that in adult rats exposed to soman, treatment with both therapeutic agents (LY293558 and CRM) is superior to treatment with LY293558 alone, and provides more complete protection against soman-induced seizures, neurodegeneration.

Example 4—Combination Treatment of Immature Soman-Exposed Rats Improves Behavioral Outcomes In this example, LY293558 and CRM were used to treat soman exposure in 21 day old (P21) rats in order to obtain preclinical data on the efficacy of the combination therapy in a pediatric population.

P21 male and female rats were treated with LY293558 and/or CRM at 60 minutes after 1.2×LD$_{50}$ (74.4 µg/kg; LD$_{50}$=62 µg/kg in immature rats) injection of soman. Seizure severity and duration were monitored, while neuronal loss and degeneration, abnormal development (such as atrophy) of different brain regions, and/or the development of pathophysiological and behavioral deficits were determined at different time points post-exposure, as reflected in the data discussed below.

Figures 4A, 4B, 4C:
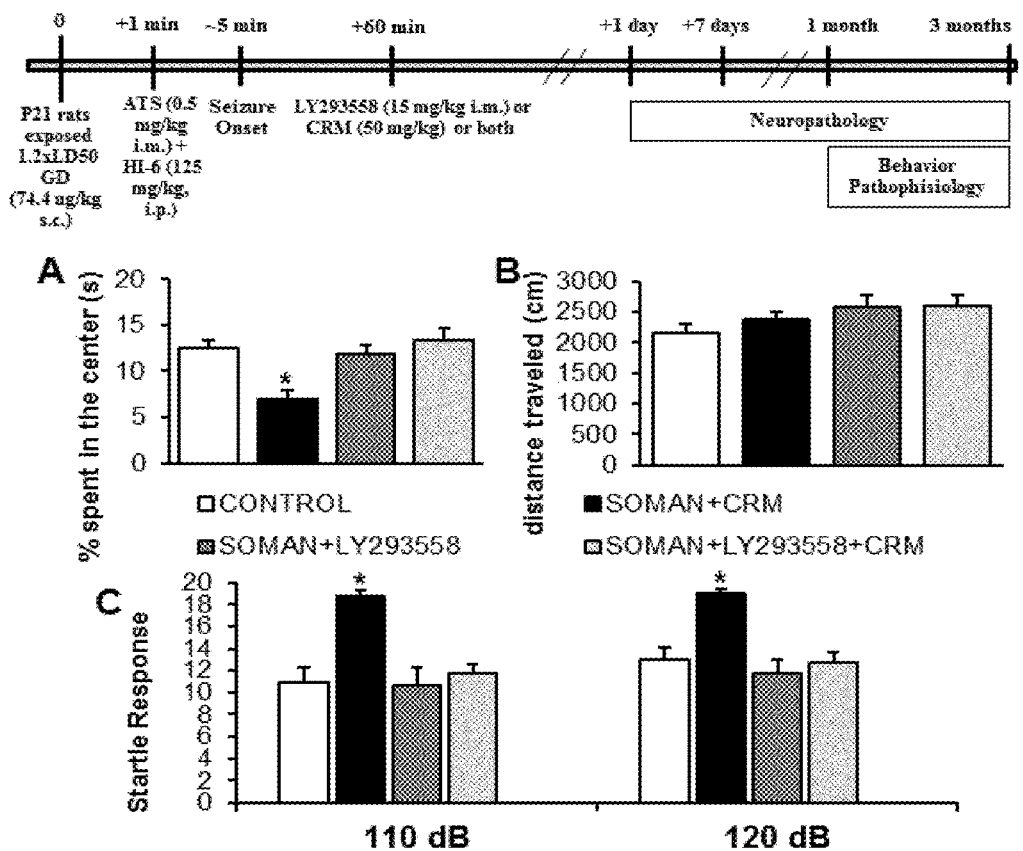
FIG. 4A-4C includes a schematic diagram of a study protocol and results in a rat model, showing that treatment with LY293558 alone or both LY293558 and CRM, but not CRM alone, prevented increase in anxiety 1 month after soman-induced SE. Similar results were obtained at the 3 month time point (not shown).

Referring to the protocol outlined in FIG. 4, P21 rats were exposed to $1.2 \times LD_{50}$ (74.4 µg/kg s.c.) of soman. Animals were treated with atropine sulfate (ATS) (0.5 mg/kg intramuscularly) and an acetylcholinesterase reactivator (HI-6) (125 mg/kg intraperitoneally) at 1 minute post-exposure, for control of the peripheral cholinergic effects. Seizure onset was observed 5 minutes after exposures. The animals were administered LY293558 (15 mg/kg intramuscularly) and/or CRM (50 mg/kg intramuscularly) 60 minutes after soman exposure. Results are shown in FIGS. 4A-4B. As seen in those figures, treatment with both therapeutic compounds, or with LY293558 alone, reduced development of pathophysiological and behavioral deficits.

The Med Associates Acoustic Response Test System (Med Associates, Georgia, Vt.), which consists of a weight-sensitive platform inside an individual sound-attenuating chamber containing a ventilated fan to provide background noise, was used to assess the acoustic startle response. Movements in response to stimuli were measured as a voltage change by a strain gauge inside each platform. Startle stimuli consisted of 110 or 120 dB sound pressure level noise bursts of 20-millisecond duration. Responses were recorded by an interfaced Pentium computer as the maximum response occurring during the no-stimulus periods, and during the startle period, and were assigned a value based on an arbitrary scale used by the software of the Test System. Results are shown in FIG. 4C.

A similar experiment was carried out in 12 day old rats, which correspond to human newborns. P12 rats were exposed to $1.2 \times LD_{50}$ (32.4 µg/kg s.c.) of soman. Animals were treated with atropine sulfate (ATS) (0.5 mg/kg intramuscularly) and an acetylcholinesterase reactivator (HI-6) (125 mg/kg intraperitoneally) at 1 minute post-exposure, for control of the peripheral cholinergic effects. Seizure onset was observed 5 minutes after exposures. The animals were administered LY293558 (10 mg/kg intramuscularly) and/or CRM (50 mg/kg intramuscularly) 60 minutes after soman exposure. Results are shown in FIGS. 23A-23C, FIGS. 24A-24B, FIGS. 25A-25C, and FIGS. 26A-26B. As seen in those figures, treatment with both therapeutic compounds, or with LY293558 alone, reduced development of pathophysiological and behavioral deficits at 30 days (FIGS. 23A-23C) and 3 months (FIGS. 25A-25C) post soman exposure. These results additionally show that LY293558 alone or the combination of LY293558 and caramiphen prevented the reduction in charge transferred by $GABA_A$ receptor-mediated spontaneous IPSCs 30 days after exposure to soman (FIGS. 24A-24B) and 3 months after soman exposure (FIGS. 26A-26B).

Considering the pronounced NMDA receptor activity in immature animals—which may be centrally responsible for the high seizure susceptibility of the immature brain—as well as the role of NMDA receptors in excitotoxicity, the benefit provided by treatment with both LY293558 and CRM to immature animals is significant.

Example 5—Combination Treatment of Immature Soman-Exposed Rats Improves Survival And Seizure Control P21 rats were exposed to $1.2 \times LD_{50}$ soman (74.4 µg/kg, s.c.) and treated with ATS (0.5 mg/kg, i.m.) and HI-6 (125 mg/kg, i.p.) as outlined in Example 4. One hour after exposure, animals were administered LY293558 (20 mg/kg, i.m.) and/or CRM (50 mg/kg, i.m.). Results are shown in FIG. 5.

As shown in FIG. 5, animals treated with both therapeutic compounds exhibited the highest 24-hour survival rates (95%) and seizure control (100%), with a pronounced reduction in latency to seizure control (13±4 min compared to 25±3 min for LY293558 alone).

A similar experiment was performed in P12 rats, which correspond to newborn human. P12 rats were exposed to $1.2 \times LD_{50}$ soman (32.4 µg/kg, s.c.) and treated with ATS (0.5 mg/kg, i.m.) and HI-6 (125 mg/kg, i.p.) as outlined in Example 4. One hour after exposure, animals were administered LY293558 (10 mg/kg, i.m.) and/or CRM (50 mg/kg, i.m.). Results are shown in FIG. 21.

As shown in FIG. 21, newborn animals treated with both therapeutic compounds exhibited 100% 24-hour survival rates and seizure control, with a pronounced reduction in latency to seizure control (18±5 min compared to 35±6 min for LY293558 alone).

Example 6—Combination Treatment of Immature Soman-Exposed Rats Reduces Seizure Severity P21 rats were exposed to $1.2 \times LD_{50}$ soman (74.4 µg/kg, s.c.) and treated with ATS (0.5 mg/kg, i.m.) and HI-6 (125 mg/kg, i.p.) as outlined in Example 4. One hour after exposure, animals were administered LY293558 (20 mg/kg, i.m.) and/or CRM (50 mg/kg, i.m.). Results are shown in FIG. 6.

Figure 6:
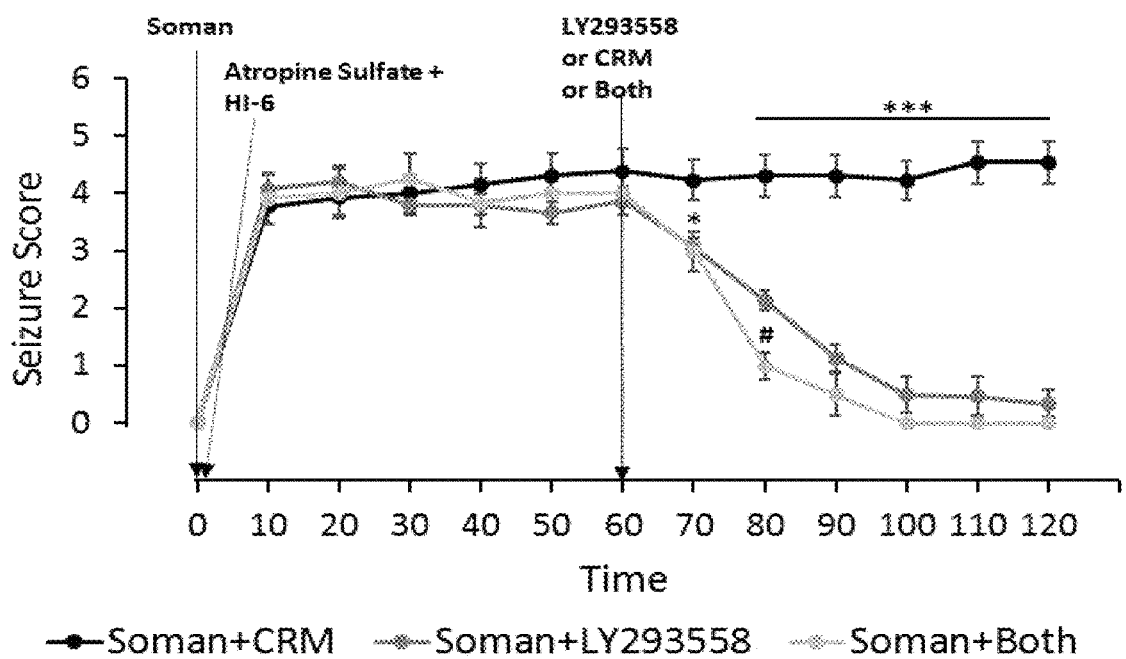
FIG. 6 shows that treatment with LY293558 and CRM reduces the severity of soman induced seizures faster than either compound alone in a rat model. CRM alone, at a dose of 50 mg/kg, was not effective in reducing seizure severity within 120 min after exposure.

As shown in FIG. 6, treatment with LY293558 and CRM reduces the severity of soman induced seizures faster than either compound alone in immature rats. CRM alone, at a dose of 50 mg/kg, was not effective in reducing seizure severity within 120 min after exposure.

Collectively, Examples 4-6 show that in the P21 rats exposed to soman, treatment with both therapeutic agents was superior to treatment with LY293558 alone, as it stopped seizures significantly faster and increased survival. This suggests that soman-induced damage of the amygdala and the hippocampus, as well as behavioral deficits, are prevented by the combination treatment.

Example 7—Combination Treatment of Immature Soman-Exposed Rats Reduces Neurodegeneration in the Amygdala P21 rats were exposed to $1.2 \times LD_{50}$ soman (74.4 µg/kg, s.c.) and treated with ATS (0.5 mg/kg, i.m.) and HI-6 (125 mg/kg, i.p.) as outlined in Example 4. One hour after exposure, animals were administered LY293558 (20 mg/kg, i.m.) and/or CRM (50 mg/kg, i.m.). Animals were monitored for up to 3 months: control animals (n=7), soman-exposed animals that received CRM (50 mg/kg) at 60 minutes post-exposure (n=10), soman-exposed animals that received LY293558 (20 mg/kg) at 60 minutes after soman-injection (n=10) and soman-exposed animals that received both LY293558 and CRM at 60 minutes after soman-injection (n=10).

Figures 7A, 7B:
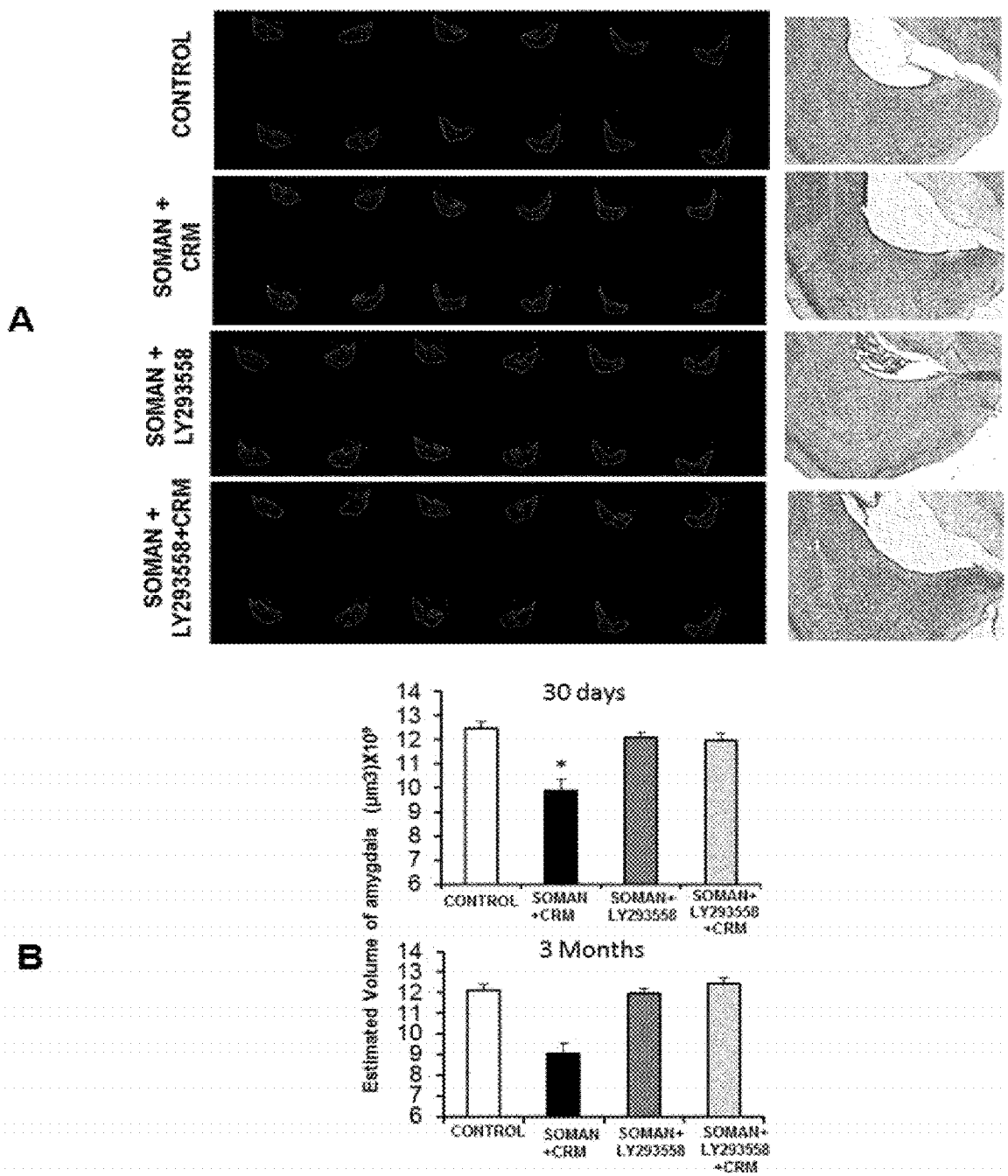
FIG. 7A-7B show the effects of soman exposure on the amygdala 30 days and 3 months after exposure in a rat model.

Degeneration of the amygdala was significantly reduced in animals treated with both LY293558 and CRM, as shown in FIG. 7. For example, FIG. 7B shows group data of the estimated volume of amygdala for each treatment group, 30 days after the exposure (top) and 3 months after the exposure (bottom), with CRM alone failing to prevent degeneration of the amygdala.

Example 8—Combination Treatment of Immature Soman-Exposed Rats Reduces Neurodegeneration in the Hippocampus P21 rats were exposed to 1.2×LD$_{50}$ soman (74.4 µg/kg, s.c.) and treated with ATS (0.5 mg/kg, i.m.) and HI-6 (125 mg/kg, i.p.) as outlined in Example 4. One hour after exposure, animals were administered LY293558 (20 mg/kg, i.m.) and/or CRM (50 mg/kg, i.m.).

Animals were monitored for up to 3 months: control animals (n=7), soman-exposed animals that received CRM (50 mg/kg) at 60 minutes post-exposure (n=10), soman-exposed animals that received LY293558 (20 mg/kg) at 60 minutes after soman-injection (n=10) and soman-exposed animals that received both LY293558 and CRM at 60 minutes after soman-injection (n=10).

Figures 8A, 8B:
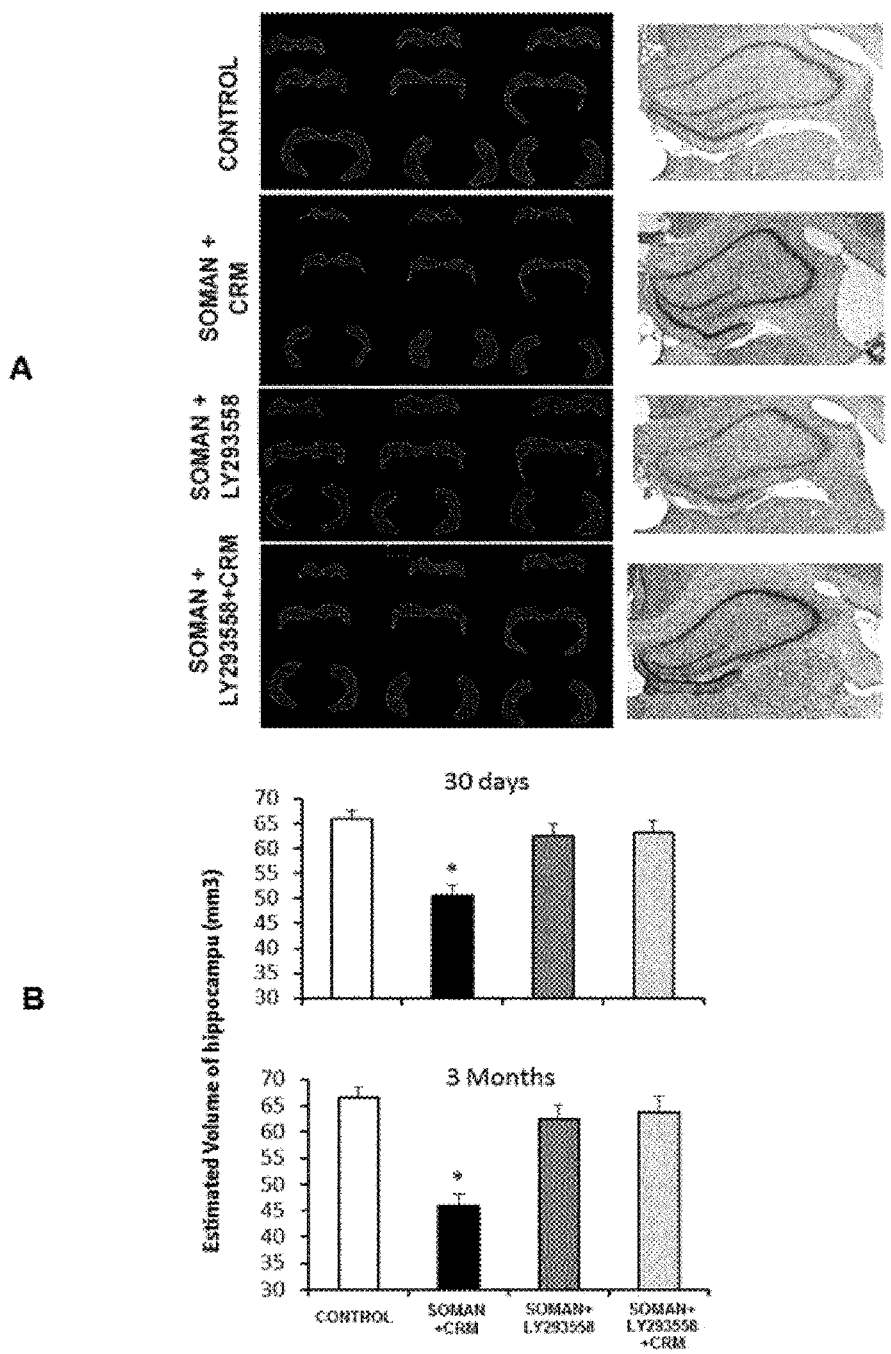
FIGS. 8A-8B show the effects of soman exposure on the hippocampus 30 days and 3 months after exposure in a rat model.
Figure 9:
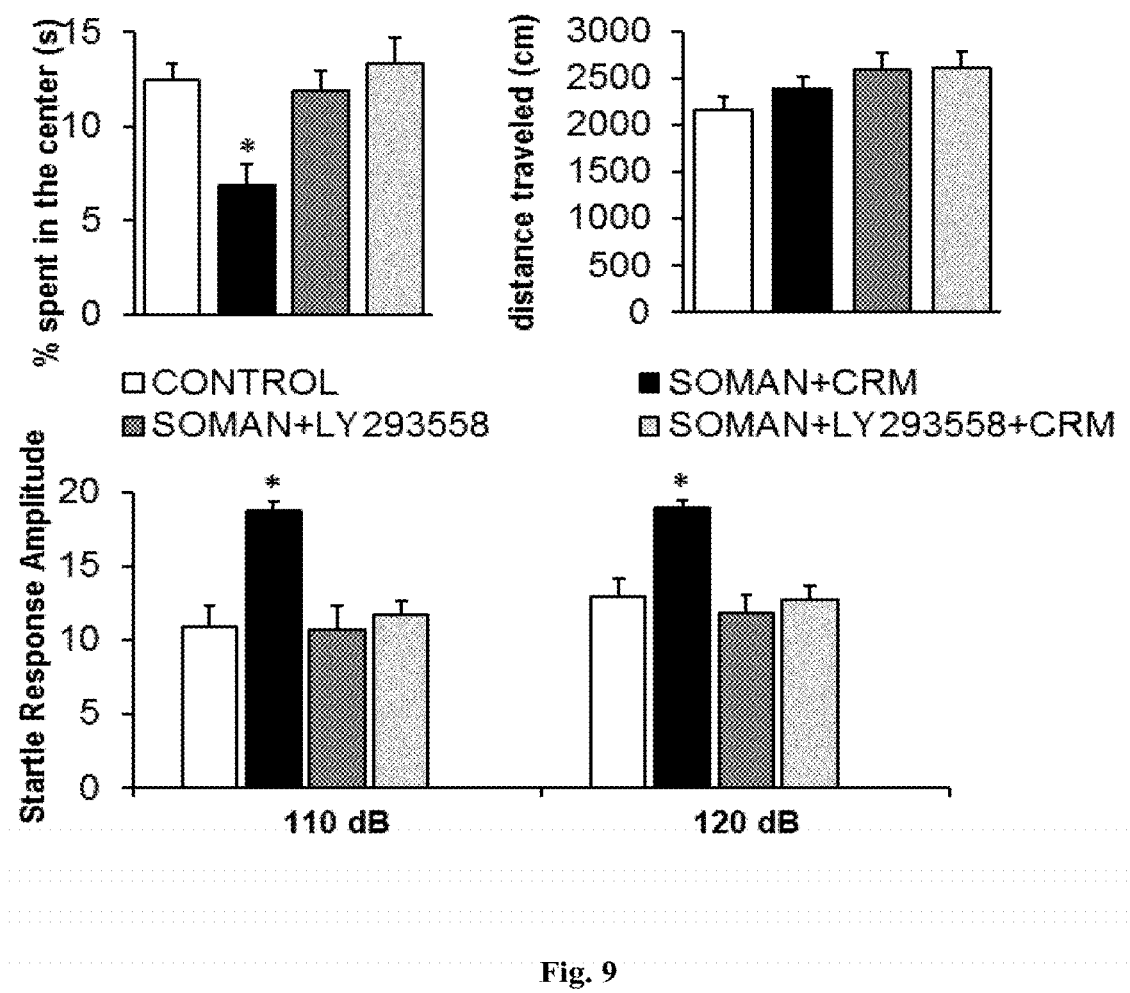
FIG. 9 shows that treatment with LY293558 and CRM reduced anxiety in open field and acoustic startle response tests 30 days after exposure to soman in a rat model, as shown by % time spent in the center of the open field, distance travelled, and Startle Response Amplitude, for the control group (n=14), soman-exposed rats who received CRM (n=16), similarly treated rats who received LY293558 at 60 minutes after soman exposure (n=13), and rats who received both LY293558 and CRM (n=14).
Figure 10:
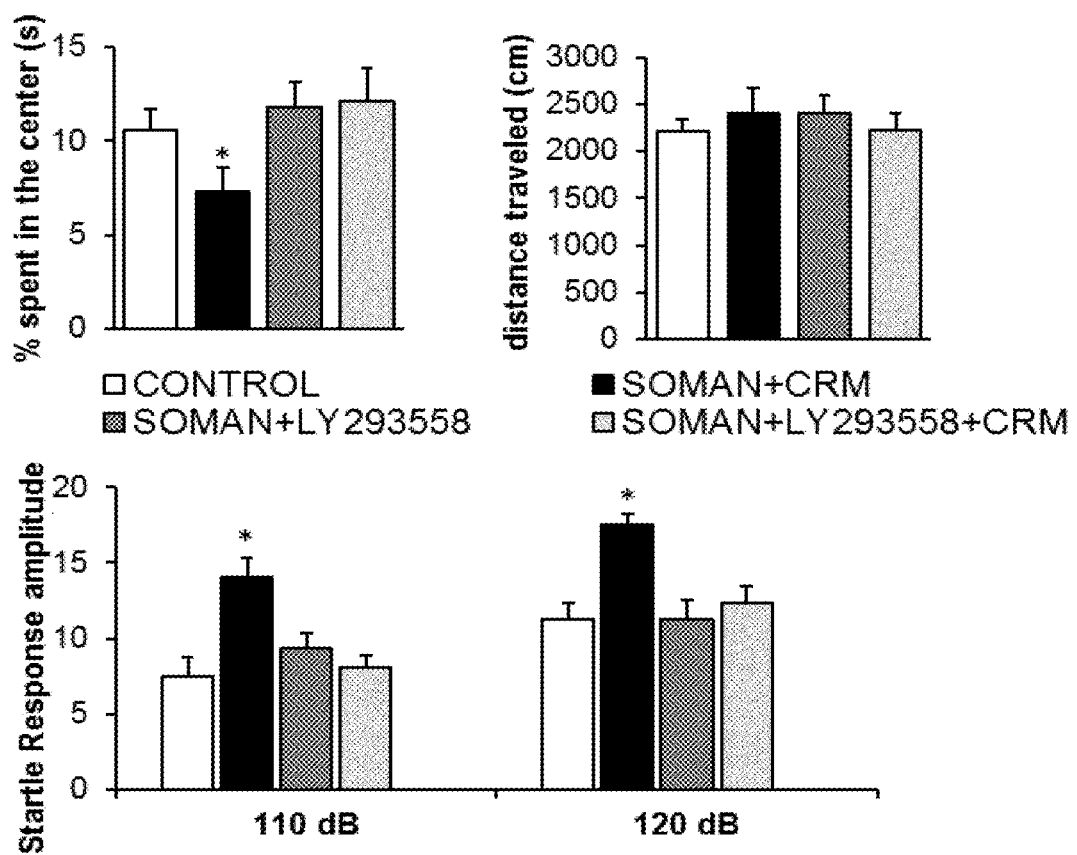
FIG. 10 shows that treatment with LY293558 and CRM reduced anxiety in open field and acoustic startle response tests 3 months after exposure to soman, as shown by: % time spent in the center of the open field and distance travelled, and Startle Response Amplitude, for the control group (n=12), soman-exposed rats who received CRM (n=13), similarly treated rats who received LY293558 at 60 minutes after soman exposure (n=13), and for rats who received combination of LY293558 and CRM (n=12).

Degeneration of the hippocampus was significantly reduced in animals treated with both LY293558 and CRM, as shown in FIG. 8. For example, FIG. 8B shows group data of the estimated volume of the hippocampus for each treatment group, 30 days after exposure (top) and 3 months after exposure (bottom), with CRM alone failing to prevent degeneration of the hippocampus.

Example 9—Acoustic Startle Response Testing in Immature Rats 30 Days Post-Soman Exposure P21 rats were treated according to the protocol outlined in Example 4 and then assessed for acoustic startle response at 30 days post-soman exposure using the Med Associates Acoustic Response Test System outlined in Example 4.

The results of this study showed that treatment with LY293558 and CRM reduced anxiety in open field and acoustic startle response tests 30 days after exposure to soman, as shown by % time spent in the center of the open field, distance travelled, and Startle Response Amplitude, for the control group (n=14), soman-exposed rats who received CRM (n=16), similarly treated rats who received LY293558 at 60 minutes after soman exposure (n=13), and rats who received both LY293558 and CRM (n=14).

Example 10—Acoustic Startle Response Testing in Immature Rats 3 Months Post-Soman Exposure P21 rats were treated according to the outlined in Example 4 and then assessed for acoustic startle response at 3 months post-soman exposure using the Med Associates Acoustic Response Test System outlined in Example 4.

The results of this study showed that treatment with LY293558 and CRM reduced anxiety in open field and acoustic startle response tests 3 months after exposure to soman, as shown by % time spent in the center of the open field and distance travelled, and Startle Response Amplitude, for the control group (n=12), soman-exposed rats who received CRM (n=13), similarly treated rats who received LY293558 at 60 minutes after soman exposure (n=13), and for rats who received combination of LY293558 and CRM (n=12).

Results of Examples 9 and 10 show that treatment with both therapeutic compounds significantly reduced anxiety (a marker of behavioral changes) at 30 days and 3 months post-exposure to soman, respectively.

Example 11—Electrophysiology Studies

P21 rats were treated according to the protocol outlined in Example 4 and then electrophysiology studies were performed in in vitro brain slices (400 µm thick) containing the amygdala of the treated rats.

The slice medium consisted of (in mM): 125 NaCl, 2.5 KCl, 1.25 NaH$_2$PO$_4$, 21 NaHCO$_3$, 2 CaCl$_2$, 1 MgCl$_2$, and 11 D-glucose. For whole-cell recordings of spontaneous inhibitory post-synaptic currents (IPSCs) from principal BLA neurons, the patch electrodes had resistances of 3.5-4.5 MΩ when filled with the internal solution: 60 mM CsCH$_3$SO$_3$, 60 mM KCH3SO3, 10 mM KCl, 10 mM EGTA, 10 mM HEPES, 5 mM Mg-ATP, 0.3 mM Na$_3$GTP (pH 7.2), 290 mOsm.

Recorded currents were amplified and filtered (1 kHz) using the Axopatch 200B amplifier (Axon Instruments, Foster City, Calif.). Field potentials were evoked by stimulation of the external capsule at 0.05 Hz. Recording glass pipettes were filled with ACSF (resistance ~5 MΩ). For both whole-cell and field potential recordings, signals were digitized using the pClamp 10.2 software (Molecular Devices, Union City, Calif.).

Figure 11A:
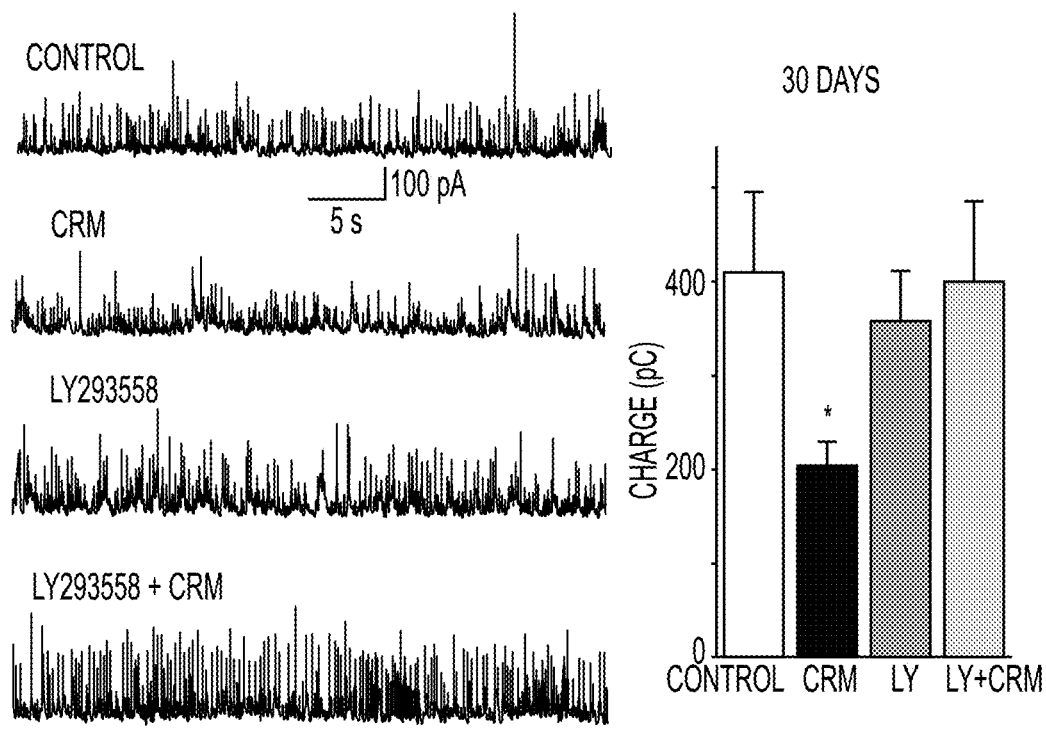
FIGS. 11A-11B show that treatment with LY293558 and CRM prevented a reduction in charge transferred by $GABA_A$ receptor-mediated spontaneous IPSCs s recorded from principal cells of the basolateral amygdala, 30 days (FIG. 11A) and 3 months (FIG. 11B) after exposure to soman. The left panels show example current traces in v-clamp mode. GABAaRs-mediated sIPSCs were recorded at +30 mV holding potential. The right panels show charge [pico-Coulombs; pC] transferred by sIPSCs of BLA principal neurons during a 40 second time window. For the 30 day time point: Control: 413.23±84.19 (n=7); CRM treated: 201.49±30.91 (n=7); LY293558 treated: 359.1±53.98 (n=8); LY293558+CRM treated: 402.57±85.86 (n=13). * $p<0.05$ compared to Control (independent t-test). For the 3 month time point: Control: 669.94±124.59 (n=10); CRM treated: 378.68+−40.67 (n=7); LY293558-treated: 627.89±119.90 (n=7); both LY293558- and CRM-treated: 683.22±136.41 (n=6). * $p<0.05$ compared to Control (independent t test).
Figure 11B:
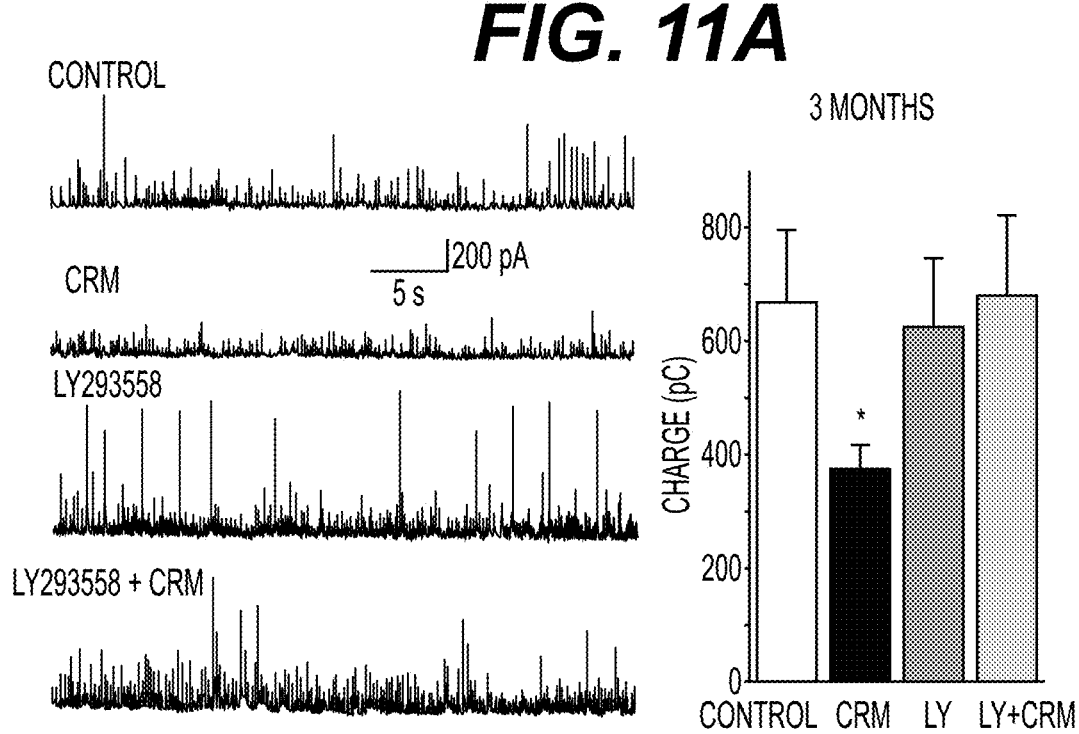

Results are shown in FIG. 11, which indicate that treatment with both therapeutic agents prevented a reduction in charge transferred by GABA$_A$ receptor mediated spontaneous IPSCs 30 days (FIG. 11A) and 3 months (FIG. 11B) post exposure to soman.

Collectively, the results of Examples 4-11 demonstrate the efficacy of the methods described herein in immature rats exposed to soman, indicating that the methods will be effective for treating children exposed to nerve agents. Treatment with both therapeutic agents (LY293558 and CRM) was superior to treatment with LY293558 alone, providing more complete protection against soman-induced seizures, neurodegeneration, and behavioral deficits, and also providing a very rapid recovery from the toxic effects of exposure.

Example 12—Use of LY293558 in Treating AMPA Induced Seizures

LY293558 was evaluated in a mouse seizure model where seizures were induced by intracerebral injection of S-alpha-amino-3-hydroxy-5-methyl-4-isoxazole proprionate (S-AMPA, 1.25 nmol), a dose and route known to induce seizures within minutes in 90-100% of treated animals. LY293558 is also known to be an antagonist at the AMPA receptor and was administered intravenously at 1, 3, 10 and 30 mg/kg 15 minutes prior to the S-AMPA and found to dose dependently reduce proportion of animals experiencing seizures with an ED50 calculated to be 2.95 mg/kg.

The results indicate that LY293558 exhibits pharmacologic effects that could reduce seizures induced by neurotransmitters known to induce seizures. The addition of an NMDA receptor antagonist (e.g., caramiphen), and, optionally, midazolam, to the treatment regimen could further potentiate the observed pharmacological effects of LY293558.

Example 13—Use of LY293558 in Treating Opiate Withdrawal Symptoms

LY293558 was evaluated in a drug withdrawal model in morphine dependent rats. Morphine dependence was induced by subcutaneous implantation of morphine containing pellets daily for two days and allowing another 48 hours for continual morphine absorption. Withdrawal was induced by removing the morphine pellets followed by administration of the opioid antagonist naloxone. LY293558 was prophylactically administered (1, 10 or 30 mg/kg, s.c.) at 15 minutes prior to precipitating withdrawal with the naloxone. A panel of known withdrawal behaviors was scored over a 1 hour observation period. A composite withdrawal score showed a dose dependent improvement in withdrawal symptoms.

Individual withdrawal symptoms such as ptosis, chewing, diarrhea, stereotyped head movements and writhing were all statistically significantly reduced at the 10 mg/kg dose of LY293558. Additional symptoms of wet dog shakes, lacrimation and salivation were significantly reduced at the 30 mg/kg dose. Other symptoms of withdrawal including irritability, digging, jumping, chatter and erection were all nominally lower, but did not reach statistical significance. A parallel set of experiments evaluated neuronal activity in the locus coeruleus (LC) by in vivo electrophysiology in anesthetized animals. Morphine withdrawal induced an 8-fold increase (0.5 Hz to 4 Hz) in LC neuronal cell firing, an effect that was dose-dependently inhibited by LY293558 and nearly normalized (to 1 Hz) at the 10 mg/kg dose. The result is suggestive of LY293558 possessing beneficial effects for the adverse CNS consequences of opiate withdrawal.

This model indicates that LY293558 can be effectively used in substance abuse treatments, such as when LY293558 can be administered prior to withdrawal of the substance of abuse to alleviate and treat withdrawal symptoms, and also indicates that LY293558 may be useful in treating or reducing withdrawal symptoms when administered after withdrawal of the substance of abuse. The addition of an NMDA receptor antagonist (e.g., caramiphen), and, optionally, midazolam, to the treatment regimen could further potentiate the observed pharmacological effects of LY293558.

Example 14—Use of LY293558 in Treating Seizures Induced by an Illicit Drug

LY293558 was evaluated in a catecholamine depleted rat model of ambulations induced by phencyclidine (also known as "angel dust" or PCP). In these studies, catecholamines were depleted for 24 hours prior to testing and ambulations were measured by breaks in photocell beams. Subcutaneous administration of PCP dramatically increased ambulatory activity (6× over controls). In animals pretreated with LY293558 (3 mg/kg, sc) at 30 minutes prior to PCP administration, ambulations were reduced by 52%.

These results suggest glutamate receptor involvement in the ambulations occurring from exposure to PCP, and that LY293558 has activity in ameliorating seizure-like activity arising from exposure to an illicit drug of abuse. The addition of an NMDA receptor antagonist (e.g., caramiphen), and, optionally, midazolam, to the treatment regimen could further potentiate the observed pharmacological effects of LY293558.

Example 15—Use of LY293558 in Treating Seizures Induced by Direct Electrical and Additional CNS Stimuli LY293558 was evaluated in a number of seizure models in both rats and mice where seizures were induced by a variety of stimuli including electrical shock (corneal electrode), pentylenetetrazole administration, audiogenic stimuli and amygdala stimulation. LY293558 was administered prophylactically at a dose in the range of 0.3 to 30 mg/kg, s.c. at 30 minutes prior to testing. LY293558 protected against tonic-clonic seizures occurring following 60 Hz (10 of 50 mA) of corneal electrical stimulation as well as the limbic seizures occurring with the 6 Hz stimulus. In these studies an ED50 for LY293558 was determined to be 9 mg/kg, sc as a 30 minute pretreatment. In the pentylenetetrazole studies, the proportion of mice completely protected from seizure increased dose dependently by a 30 minute s.c. prophylactic pretreatment with LY293558 with an ED50 determined to be 10.3 mg/kg. When using an audiogenic stimulus (120 dB white noise, 60 s) mice were dose dependently protected from tonic extensor seizures with an ED50 of 1.9 mg/kg, s.c. as a 30 minute pretreatment. In contrast, LY293558 was ineffective in altering the threshold stimulus for evoking seizures when using direct stimulation of the amygdala via implanted electrodes.

These results suggest that LY293558 is effective at protecting from seizures arising from a variety of triggers except for the amygdala kindling model where it may have been impossible for a pharmacologic agent to antagonize direct electrical stimulation to one of the seizure centers of the brain (amygdala). The results also suggest that LY293558 can reduce seizures triggered by either pharmacologic (phentylenetetrazole) or remote (corneal or audiogenic) stimulus, but not when depolarizing currents are delivered directly to the amygdala. The addition of an NMDA receptor antagonist (e.g., caramiphen), and, optionally, midazolam, to the treatment regimen could further potentiate the observed pharmacological effects of LY293558.

Example 16—Delayed LY293558 (1 Hour) Reduces Soman-Induced Mortality, Seizures and Neuropathology without Use of a Benzodiazepine LY293558 was evaluated in a rat model of a G-series nerve agent, soman (GD), exposure. Soman was administered via a single subcutaneous injection (154 mcg/kg, or 1.4×LD50. To increase survival rate, rats were administered HI-6 (1-(2-hydroxyiminomethylpyridinium)-3-(4-carbamoylpyridinium)-2-oxapropane dichloride; 125 mg/kg i.p.) at 30 minutes before soman exposure. HI-6 is a bispyridinium oxime (similar to pralidoxime) that reactivates inhibited acetylcholinesterase. Within 1 minute after soman exposure, rats also received an intramuscular injection of atropine sulfate (2 mg/kg) One hour after soman exposure, a group of rats was administered LY293558 (50 mg/kg, intraperitoneal) and were compared to soman-exposed rats that received HI-6 and atropine but did not receive LY293558 (soman only control arm). A subset group of animals was implanted with electrodes for EEG documented seizure monitoring 1 week prior to soman exposure. Survival in non-EEG electrode animals for LY293558 recipients was 100% (12 of 12) versus 55% (11 of 20) in the group that did not receive LY293558 This difference in survival rate was statistically significant (p<0.01; Pearson's chi-square and Friedman's exact test). In animals which had prior EEG electrode implants, survival was only nominally higher in the LY293558 group (67%; 10 of 15) versus 54% in the control group (6 of 11).

Figure 12:
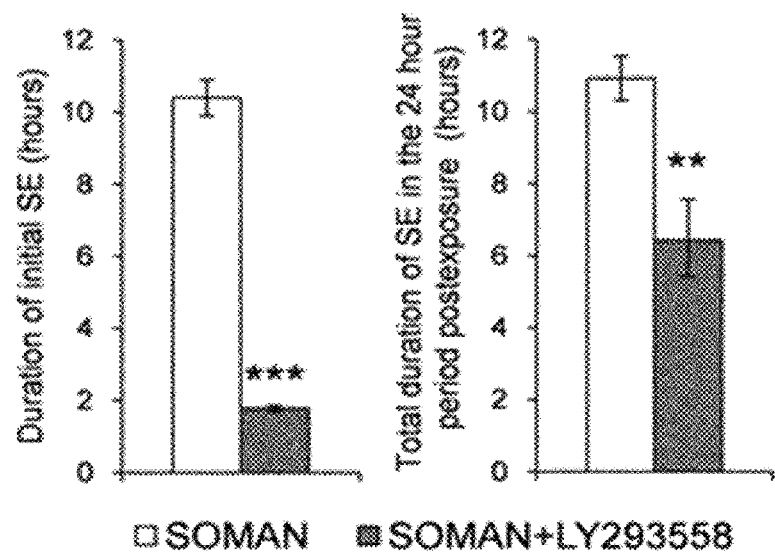
FIG. 12 shows suppression of initial status epilepticus (SE) with LY293558 and significant suppression over 24 hours. Soman (n=4) and soman+LY293558 (n=7).  $p<0.01$ and * $p<0.001$ by unequal variance t-test.

As shown in FIG. 12, the initial status epilepticus (SE) that develops within 5-15 minutes following exposure to soman was dramatically reduced with LY293558 vs. control group where SE continued for approximately 10 hours before spontaneously resolving. When measured over a 24 hour period, total duration of SE was significantly reduced with LY293558.

Figure 13:
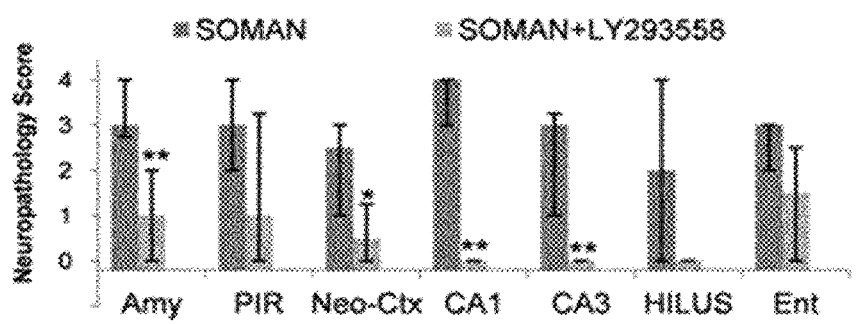
FIG. 13 shows protection against neuronal damage in the subcortex and a neocortical sample region by LY293558 administration, in rats studied at day 7 following soman exposure. Soman (n=6) and soman+LY293558 (n=6). Subcortical regions evaluated include amygdala (Amy), piriform cortex (PIR), neocortex (Neo-Ctx), CA1 and CA3 regions of the hippocampus, the hilus and entorhinal cortex (Ent). * $p<0.05$ and ** $p<0.01$ by Mann-Whitney U test.

Brains from a select group of animals that were maintained until either 1 or 7 days post soman exposure were processed for histopathology with staining by Nissl and Fluoro Jade C. As shown in FIG. 13, a neuropathology scoring system (0-4; as none, minimal, mild, moderate or severe) was used to assess neuronal damage (cells staining positive with FJC) in subcortical regions of the brain in animals 7 days following soman exposure. The neuropathology score ranged from mild-to-moderate in regions studied. Treatment with LY293558 resulted in nominal protection observed in all regions, a finding that was statistically significant in many regions of the subcortex. The addition of an NMDA receptor antagonist (e.g., caramiphen), and, optionally, midazolam, to the treatment regimen could further potentiate the observed pharmacological effects of LY293558

Example 17—Early LY293558 (20 Minute) Reduces Soman-Induced Mortality, Seizures and Neuropathology Without Use of a Benzodiazepine LY293558 was evaluated in a rat model of a G-series nerve agent, soman (GD), exposure. Soman was administered via a single subcutaneous injection (132 mcg/kg, which is approximately 1.2×LD50). To increase survival, twenty minutes after soman exposure, all rats received an intramuscular injection of 2 mg/kg atropine sulfate as well as an intraperitoneal injection of 125 mg/kg HI-6. In contrast to Example 16, in this study LY293558 was administered earlier (20 minutes from soman exposure vs. 1 hour), at a lower dose (15 mg/kg versus prior 50 mg/kg) and by an intramuscular route (vs. prior intraperitoneal). LY293558 treated rats were compared to animals receiving soman exposure, atropine and HI-6.

Survival in non-EEG electrode animals for LY293558 recipients was 100% (18 of 18) versus 64% (18 of 28) in the group that did not receive LY293558 This difference in survival rate was statistically significant (p<0.01; Pearson's chi-square).

Figure 14:
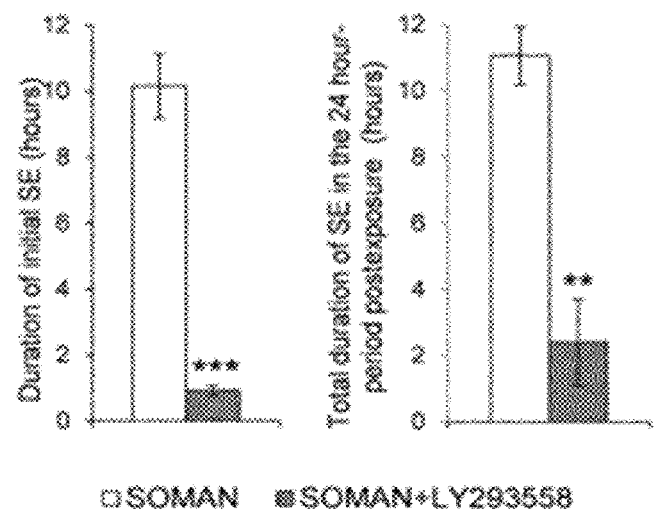
FIG. 14 shows suppression of initial status epilepticus (SE) with LY293558 and significant suppression over 24 hours. Soman (n=5) and soman+LY293558 (n=8).  $p<0.01$ and * $p<0.001$ by unequal variance t-test.

As shown in FIG. 14, the initial status epileptics (SE) that develops within minutes following exposure to soman was dramatically reduced with LY293558 vs. control group where SE continued for approximately 10 hours before spontaneously resolving. When measured over a 24 hour period, total duration of SE was significantly reduced with LY293558.

Figure 15:
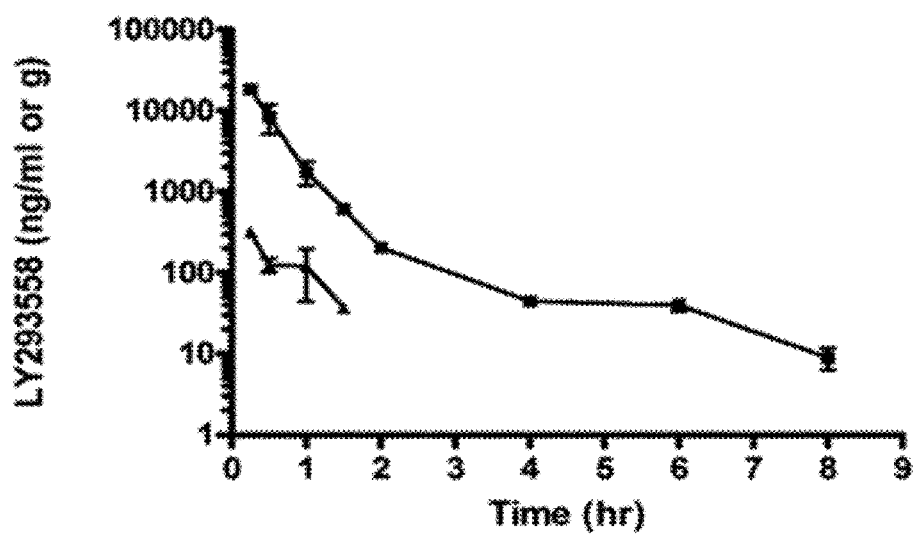
FIG. 15 shows plasma and brain levels of LY293558 following 15 mg/kg Intramuscular injection. Plasma levels (squares) and brain levels (triangles) of LY293558 following 15 mg/kg, intramuscular. Plasma samples sizes are n=3-6 per time point and brain samples are n=3 per time point. Data are mean +/−standard deviation.

In this study, a small cohort of animals were reserved for pharmacokinetic assessment of LY293558. As shown in FIG. 15, LY293558 is measurable in the plasma and brain shortly (15 minutes) after intramuscular administration and remain measurable to the final time point at 8 hours.

Figure 16:
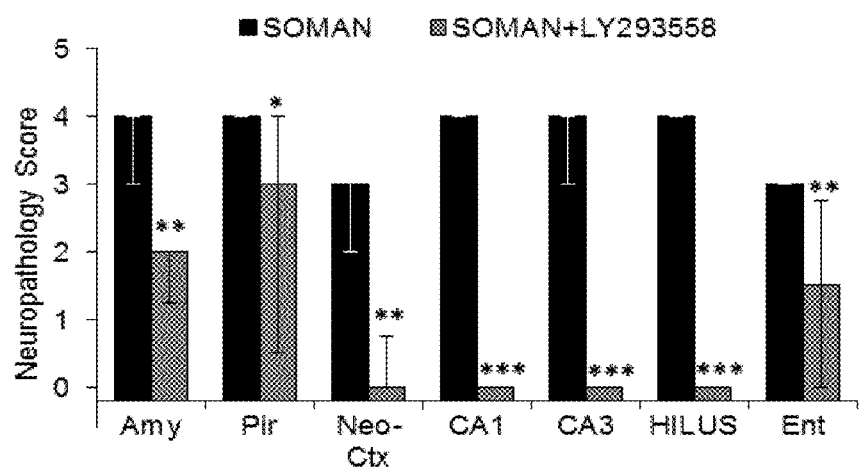
FIG. 16 shows protection against neuronal damage in the subcortex and a neocortical sample region, with LY293558 in rats studied at day 7 following soman exposure. Soman (n=18) and soman+LY293558 (n=18). Brain regions evaluated include amygdala (Amy), piriform cortex (PIR), neocortex (Neo-Ctx), CA1 and CA3 regions of the hippocampus, the hilus and entorhinal cortex (Ent). * $p<0.05$,  $p<0.01$ and  $p<0.001$ by Mann-Whitney U test.

Brains from a select group of animals that were maintained until either 1 or 7 days post soman exposure were processed for histopathology with staining by Nissl and Fluoro Jade C. As shown in FIG. 16, a neuropathology scoring system (0-4; as none, minimal, mild, moderate or severe) was used to assess neuronal damage (cells staining positive with FJC) in subcortical regions of the brain in animals 7 days following soman exposure. The neuropathology score ranged from mild-to-moderate in regions studied. Treatment with LY293558 resulted in statistically significant neuroprotection all regions in the subcortex. The addition of an NMDA receptor antagonist (e.g., caramiphen), and, optionally, midazolam, to the treatment regimen could further potentiate the observed pharmacological effects of LY293558.

Figures 17A, 17B:
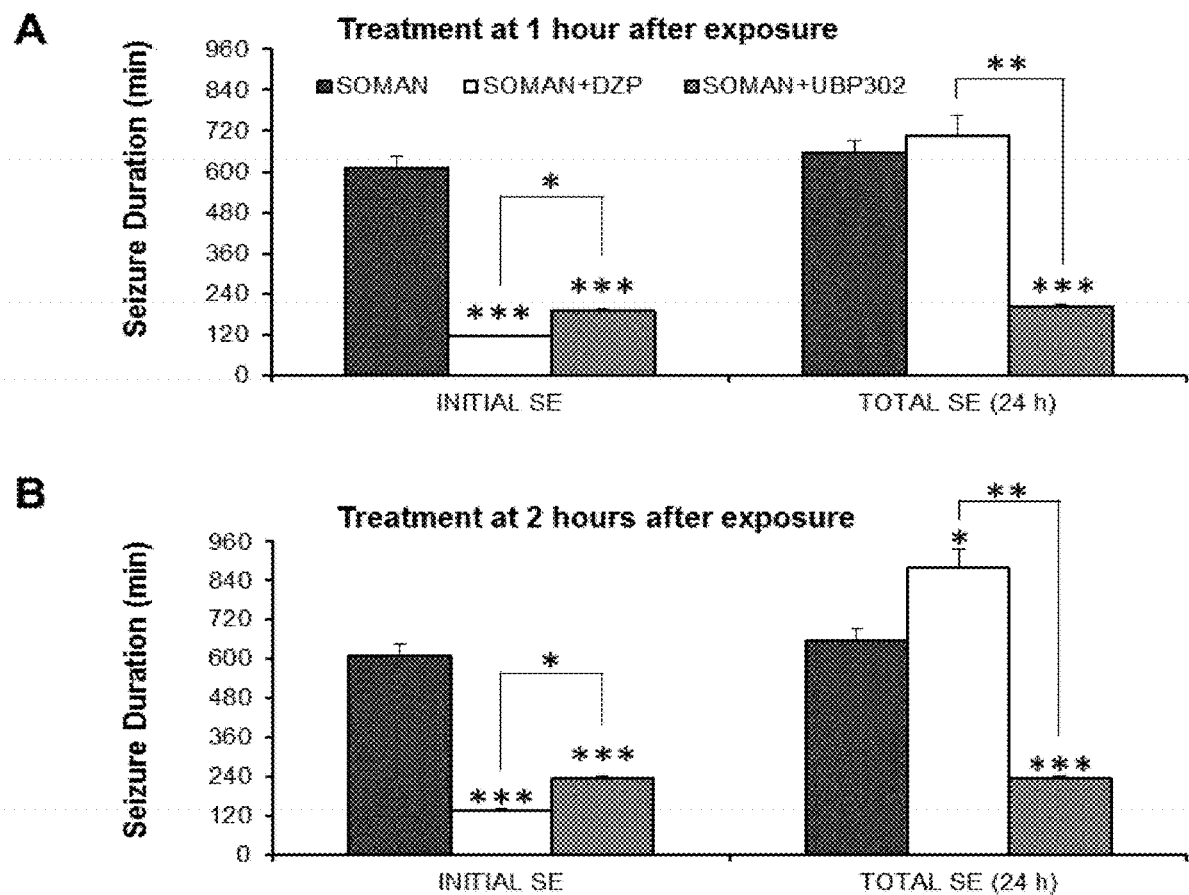
FIGS. 17A-17B show suppression of initial status epilepticus (SE) with diazepam (DZP) or UBP302 administered at 1 or 2 hours post soman exposure and significant suppression for UBP302 over 24 Hours.

Example 18—Comparison of the GluK1 Receptor Antagonist UBP302 Versus Diazepam in Soman-Induced Mortality, Seizures and Neuropathology UBP302 ((S)-3-(2-carboxybenzyl)willardiine) is a glutamate GluK1 receptor antagonist with an activity profile similar to LY293558 in nerve agent seizure models. UBP302 was studied in a soman exposure model where soman was administered via a single subcutaneous injection (154 mcg/kg, or 1.4×LD50). To increase survival rate, HI-6 was administered (125 mg/kg i.p.) at 30 minutes before soman exposure. Within 1 minute after soman exposure, rats also received an intramuscular injection of atropine sulfate. At either 1 or 2 hours post soman exposure, animals were randomly selected to receive no further treatment (soman only arm), a 20 mg/kg intramuscular dose of diazepam (soman+DZP group) or a 250 mg/kg intraperitoneal dose of UBP302 (soman+UBP group). Survival in non-EEG implanted animals was 63% (22 of 34) in the soman group and either 91% (21 of 23) for diazepam or 96% (24 of 25) for UBP302 when administered at 1 hour post soman (p<0.02 for both groups versus soman only group, Fischer exact test). The enhanced survival in both treatment groups suggests that either signaling through GABA-receptors with diazepine or inhibition of glutamate signaling with UBP302 can confer a survival benefit in this model As shown in FIG. 17, the initial status epilepticus (SE) that develops within minutes following exposure to soman was dramatically reduced with both diazepam and UBP302 when the treatment agent is administered at either 1 or 2 hours (upper panel, lower panel) following soman exposure. When measured over a 24 hour period, total duration of SE was not significantly reduced with diazepam whereas UBP302 was superior to diazepam in seizure control over 24 hours, achieving an approximate 65% suppression of seizure activity versus the soman only group. These data indicate that seizure control by antagonizing glutamate receptors is more effective at seizure suppression than stimulating GABA receptors using a benzodiazepine.

Figure 18:
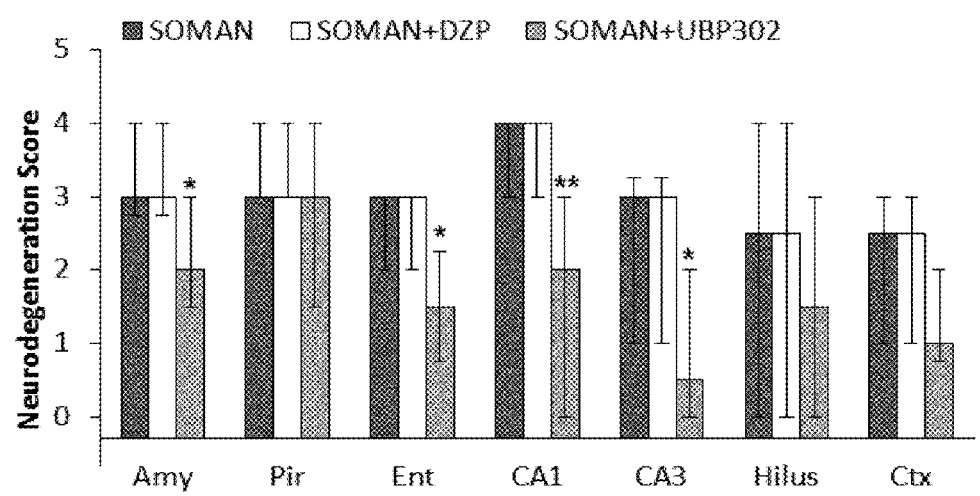
FIG. 18 shows protection against neuronal damage in the subcortex and a neocortical brain region with UBP302, and no observed neuroprotection with diazepam. Observations are n=6 for each group. Brain regions evaluated include amygdala (Amy), piriform cortex (PIR), entorhinal cortex (Ent), CA1 and CA3 regions of the hippocampus, the hilus and neocortex (Neo-Ctx), * $p<0.05$ and ** $p<0.01$ by Mann-Whitney U test.

In animals that were maintained for 7 day histopathology, UBP302, but not diazepam, administered 1 hour after soman exposure, reduced neuronal degeneration in the subcortex. As shown in FIG. 18, the amygdala, CA1, and CA3 dorsal hippocampal areas, and entorhinal cortex had reduced neuronal degeneration in the subcortex 7 days after the exposure when UBP302 was administered. The addition of an NMDA receptor antagonist (e.g., caramiphen), and, optionally, midazolam, to the treatment regimen could further potentiate the observed pharmacological effects of LY293558.

Example 19—Comparison of Delayed (1 Hour) LY293558 Versus Midazolam in Soman-Induced Mortality, Seizures, Behavioral and Pathophysiology Alterations 3 Months after Soman LY293558 was evaluated in a rat model of a G-series nerve agent, soman (GD), exposure. Soman was administered via a single subcutaneous injection (132 mcg/kg, or 1.2×LD50). To increase survival rate, rats were administered HI-6 (1-(2-hydroxyiminomethylpyridinium)-3-(4-carbamoylpyridinium)-2-oxapropane dichloride; 125 mg/kg i.p.) within 1 minute after soman exposure. HI-6 is a bispyridinium oxime (similar to pralidoxime) that reactivates inhibited acetylcholinesterase. Also, within 1 minute after soman exposure, rats received an intramuscular injection of atropine sulfate (2 mg/kg). One hour after soman exposure, a group of rats was administered LY293558 (15 mg/kg, i.m.) and another group received the midazolam (5 mg/kg i.m.). A subset group of animals was implanted with electrodes, 1 week prior to soman exposure, for EEG-documented seizure monitoring. Survival in non-EEG electrode-implanted animals for LY293558 recipients was 92% (25 of 27) versus 96% (26 of 27) in the group that received midazolam. This difference in survival rate was not statistically significant (p>0.05; Friedman's exact test).

Figure 19:
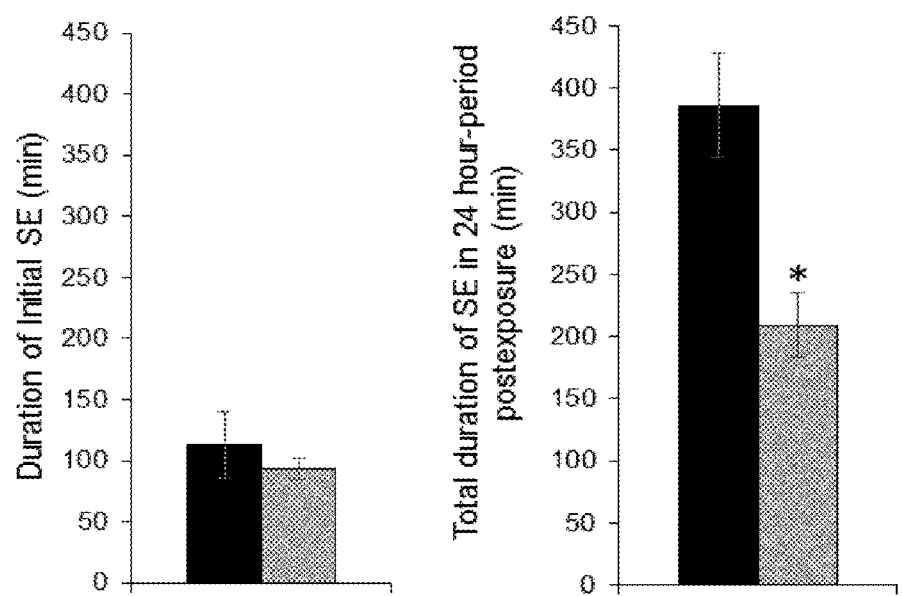
FIG. 19 shows that LY293558 produces a significantly greater reduction in the total duration of status epilepticus (SE) in the 24-h period after soman exposure in comparison to midazolam (MDZ). Soman+midazolam (n=4) and soman+LY293558 (n=4). * $p<0.05$ Student t-test.

As shown in FIG. 19, the duration of the initial status epilepticus (SE; the SE that develops within 5-15 minutes following exposure to soman and is terminated after anticonvulsant treatment) was similar in the LY293558 and the midazolam groups. However, when measured over a 24-hour period post-exposure, total duration of SE was significantly lower in the LY293558 group compared to the midazolam group (about 50% lower).

Figure 20A:
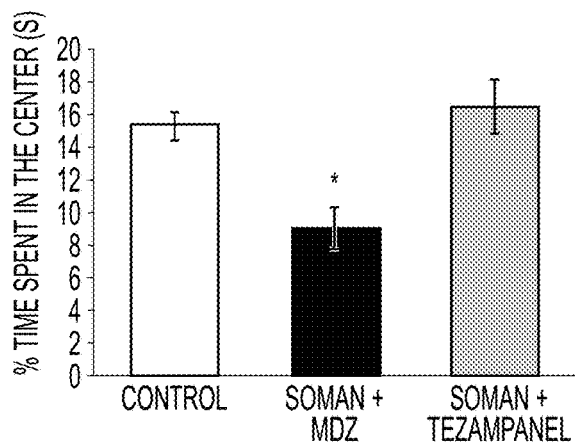
FIGS. 20A-20C show LY293558, but not midazolam, protects against soman-induced long-term increases in anxiety-like behavior as well as reduced inhibitory synaptic transmission in the Basolateral Nucleus of Amygdala (BLA), 3 months after exposure to soman.
Figure 20B:
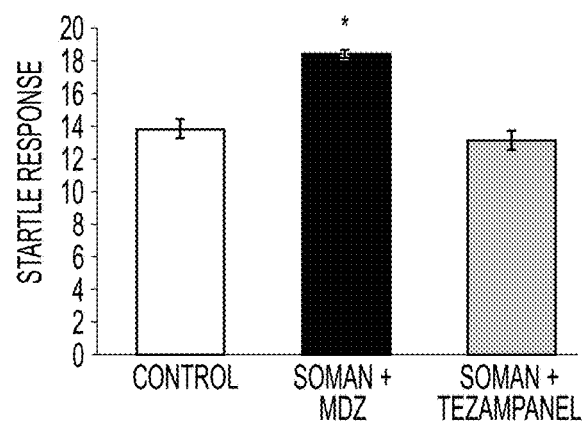
Figure 20C:
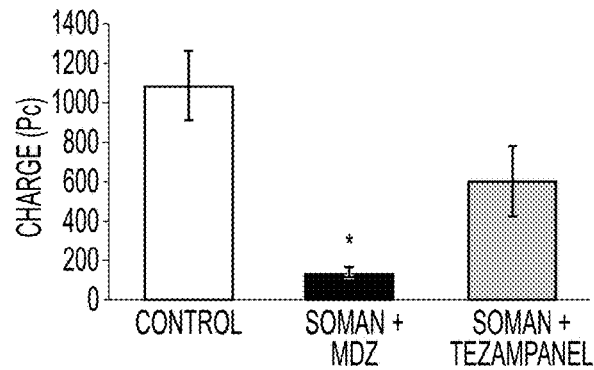

In animals that were maintained for 90 days after soman exposure, behavioral and pathophysiology tests showed that LY293558, but not midazolam treatment, prevented increases in anxiety-like behavior and exaggerated startle responses, as well as reduction in GABAergic inhibitory currents in the basolateral amygdala nucleus, as shown in FIG. 20.

The addition of an NMDA receptor antagonist (e.g., caramiphen) to the treatment regimen, and, optionally, the use of midazolam together with LY293558, could further potentiate the observed pharmacological effects of LY293558.

Example 20—Clinical Studies of LY293558 in Humans

A clinical study was conducted to determine a maximum tolerated dose (MTD) in human volunteers beginning with an i.v. bolus dose of 0.01 mg/kg. After an initial MTD was determined from n=6 volunteers the study was expanded to an additional n=16 who received escalating doses to determine an MTD for each individual. A total of 20 volunteers reached a maximum tolerated dose in a dose escalation protocol which escalated to 2.0 mg/kg i.v. bolus. The adverse events were rated as mild in all instances and include vision changes, sedation and headache. Vision changes and sedation were noted beginning at 0.9 mg/kg and headache was noted in two individuals at 1.8 mg/kg.

Additionally, an efficacy study was conducted. The study was a blinded crossover study of placebo vs. two doses of LY-293,558 at 33% and 100% of MTD where previous median MTD found to be 1.3 mg/kg. Twenty volunteers received s.c. capsaicin injections in the volar surface of the forearm and spontaneous pain, allodynia and hyperalgesia was assessed every 5 minutes for a 60 minute period. Spontaneous pain and allodynia were significantly reduced in both LY293558 groups vs. placebo. Pinprick hyperalgesia was nominally reduced at both doses and was borderline significant p=0.05 at the highest dose. Mild visual symptoms described as "looking through a haze" (or similar description) was noted in 19 of 20 volunteers (95%), and had resolved within an hour of onset. Additional side effects note included sedation (40%) and headache (10%) and also resolved within an hour.

Example 21—Postoperative Dental Pain Study in Humans

This study was a placebo controlled study of 70 patients experiencing pain following dental surgery. The study compared two i.v. doses (0.4 of 1.2 mg/kg) of LY293555 versus placebo or i.v. ketorolac (as a positive control). Pain intensity was scored multiple times with a visual analog scale over a 240 minute period. Both LY293558 and ketorolac significantly reduced pain intensity compared to placebo. Incidence of mild to moderate side effects was visual disturbance (20%), sedation (15%), headache (40%) and nausea (5%).

Example 22—Acute Migraine Study in Humans

This study was a placebo controlled study of 44 patients experiencing moderate to severe migraine symptoms. The study compared i.v. LY293555 (1.2 mg/kg) versus a placebo or subcutaneous sumatriptin as a positive control and evaluated symptoms for a 2 hour period. 54% of LY293558 reported to be pain free at 2 hours versus 60% for sumatriptin and 6% for placebo. Similar response rates were reported for nausea, photophobia and phonophobia relief. Two patients (15%) of LY293558 recipients experienced an adverse event including dizziness and sedation.

Example 23—Prophetic Alcohol and Opiate Withdrawal Phase II Trial

This example details a prospective phase II study in tremors/seizures arising from drug withdrawal (either alcohol or opiates). Withdrawal syndrome is preferred as the initial commercial indication because the market is highly concentrated (specialized rehabilitation centers), the timing of seizures can be anticipated (generally during first 72 hours of detoxification), the overall clinical course is short (detox is generally complete in 1 week) and screening failures will be virtually non-existent (not enrolled until tremors/seizures begin). While alcohol is more widely used, opiate withdrawal has become a growing concern in the U.S. The choice of which substance of abuse will be made after further consultation with key opinion leaders in the area. A small phase II study of a placebo and three dose-escalating treatment arms (40 pts/arm) would be sufficient to demonstrate anticonvulsant activity in humans. Such a study would entail administering an AMPA/GluR5(GluK1) kainate receptor antagonist (e.g., LY293558) and an NMDA receptor antagonist (e.g., caramiphen) to human subjects prophylactically, throughout detoxification, or some combination thereof in order to reduce, eliminate, or ameliorate at least one effect or symptom of alcohol or opiate withdrawal, such as withdrawal-induced seizures.

Example 24—Prophetic Neonatal Abstinence Syndrome (NAS) Phase II Trial

This examples details a prospective phase II study in NAS. NAS is a withdrawal syndrome that occurs in newborns born to mothers who are drug addicted (typically narcotics). According to recent CDC report and other data, the annual incidence is 21,000 cases per year, NAS represents up to 50% of all NICU stays, the incidence concentrates geographically (e.g., West Virginia and Vermont) as well as demographically (Native Americans). Withdrawal symptoms typically appear within the first 24-48 hours postpartum and subside inside of a week. NAS may be more attractive as an indication where successful attainment of pediatric rare disease designation and/or fast-track designation may speed the overall approval of the commercial indication. A small phase II study of a placebo and three dose-escalating treatment arms (15 neonates/arm) would be sufficient to demonstrate anticonvulsant activity in humans. Such a study would entail administering an AMPA/GluR5 (GluK1) kainate receptor antagonist (e.g., LY293558) and an NMDA receptor antagonist (e.g., caramiphen) to human infants having or suspected of having NAS prophylactically, throughout the first 24-48 postpartum period, or some combination thereof in order to reduce, eliminate, or ameliorate at least one effect or symptom of NAS, such as neurological development deficits.

Example 25—Prophetic Study of a Combination of LY293558, Caramiphen, and Midazolam to Treat Rats Exposed to Soman This examples details a prospective preclinical study of treating rats with a combination of LY293558, caramiphen, and midazolam after exposure to a nerve agent.

The study will have 3 specific aims. The first is to confirm that LY293558 in combination with caramiphen (CRM) and midazolam (MDZ) is effective in controlling sarin-induced seizures, in infant (P12), young (P21), adult (50 to 70 days-old), and aged (16 to 18 months-old) male and female rats. To accomplish this aim will require determining the $LD_{50}$ of sarin for these ages and gender of rats, and confirming that administration of LY293558+caramiphen+midazolam, 30 min after sarin exposure ($1.4 \times LD_{50}$) will reduce or prevent lethality and suppress or block seizures.

The second aim is to confirm that LY293558 in combination with caramiphen and midazolam is effective in reducing or preventing sarin-induced neuronal degeneration and neuronal loss, in infant (P12), young (P21), adult (50 to 70 days-old), and aged (16 to 18 months-old) male and female rats. Neuronal degeneration will be assessed in a number of seizure-prone brain regions, using FluoroJade-C staining. Neuronal loss will be assessed stereologically on Nissl-stained sections of the amygdala and the hippocampus. Neuropathology will be evaluated 1 day, 7 days, 1 month, and 3 months after sarin exposure.

The third aim is to confirm that LY293558 in combination with caramiphen and midazolam is effective in reducing or preventing sarin-induced pathophysiological alterations in the basolateral amygdala, as well as associated behavioral deficits, in infant (P12), young (P21), adult (50 to 70 days-old), and aged (16 to 18 months-old) male and female rats. Pathophysiology in the BLA will be assessed by studying excitability parameters in the BLA network, using whole-cell recordings in the voltage-clamp and current-clamp mode, at 1 day, 7 days, 1 month, and 3 months after sarin exposure. Two behavioral tests will be used to assess anxiety-like behavior, at 7 days, 1 month, and 3 months after sarin exposure. Correlations will be made between neuropathology, pathophysiology, and behavioral results.

The results from these studies will provide all the preclinical information necessary to confirm that administration of this combination can be effectively and safely used as a treatment for nerve agent exposure, in an emergency situation, in order to protect the people, including the more vulnerable sections of the population.

Figure 27:
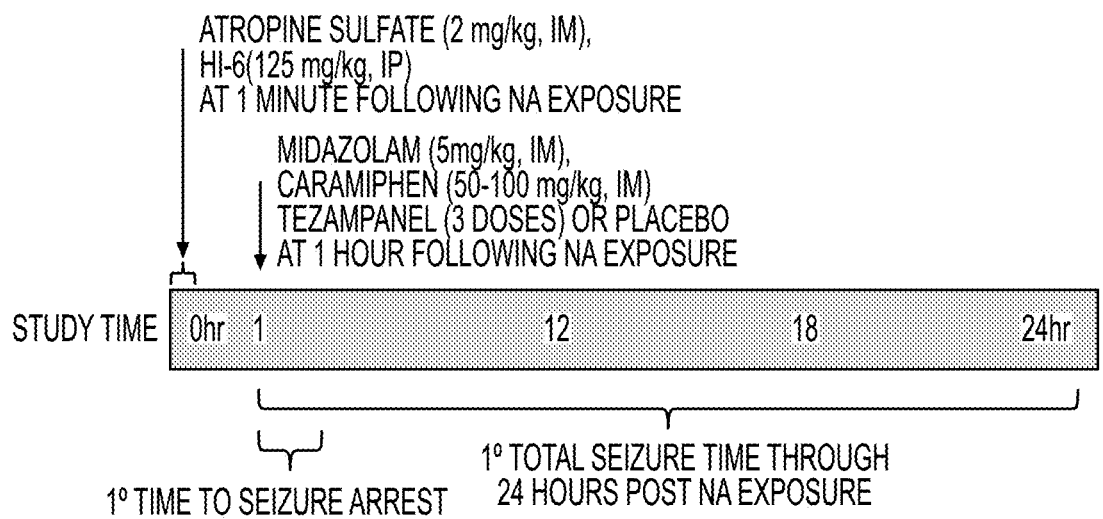
FIG. 27 shows a generalized study scheme for proposed efficacy studies of treating nerve agent exposure in 21 day old rats with a combination of LY293558, caramiphen, and midazolam.

Soman will be administered via a single subcutaneous injection (32 µg/kg, which is 1.2×LD50). To increase survival, one minute after soman exposure, all rats will receive an intramuscular injection of 2 mg/kg atropine sulfate as well as an intraperitoneal injection of 125 mg/kg HI-6. Seizures generally develop in the first 10-15 minutes following soman administration. The general study schema appears in FIG. 27.

Neuropathological analysis will be performed at 30 days, 90 days, and 6 months after soman exposure. All the procedures that will be used have been described extensively in the examples above.

Fixation & Tissue Processing. Rats will be deeply anesthetized with pentobarbital (75-100 mg/kg, i.p.) and transcardially perfused with PBS (100 ml) followed by 4% paraformaldehyde (200 ml). The brains will be removed and post-fixed overnight at 4° C., then transferred to a solution of 30% sucrose in PBS for 72 hours, and frozen with dry ice before storage at −80° C. until sectioning. Sections will be cut throughout the rostrocaudal axis of the amygdala. One series of sections will be mounted on slides (Superfrost Plus, Daigger, Vernon Hills, Ill.) in PBS for Nissl staining with cresyl violet. Adjacent series of sections will be stored at −20° C. in a cryoprotectant solution for GAD-67 immunohistochemistry. All neuropathological analysis will be done in a blind fashion.

Stereological Quantification. Design-based stereology will be used to quantify the total number of neurons in Nissl-stained sections in the BLA, at 1, 3, and 6 months after soman exposure. Sections were viewed with a Zeiss Axioplan 2ie (Oberkochen, Germany) fluorescent microscope with a motorized stage, interfaced with a computer running StereoInvestigator 9.0 (MicroBrightField). The total number of Nissl-stained neurons will be estimated using the optical fractionator probe, and, along with the coefficient of error (CE), will be calculated using Stereo Investigator 9.0 (MicroBrightField). For Nissl-stained neurons in the BLA, a 1-in-5 series of sections will be analyzed (8 sections on average). An average of 365 neurons per rat will be counted. For GABAergic interneurons immuno-labeled for GAD-67 in the BLA (see procedure below), a 1-in-10 series of sections will be analyzed (on average 6 sections). An average of 260 interneurons per rat will be counted.

GAD-67 immunohistochemistry. To label GAD-67 immunoreactive interneurons, a 1-in-5 series of free-floating sections will be collected from the cryoprotectant solution, washed three times for 5 min each in 0.1 M PBS, and then incubated in a blocking solution containing 10% normal goat serum (NGS, Chemicon International, Temecula, Calif.) and 0.5% Triton X-100 in PBS for one hour at room temperature. The sections will then be incubated with mouse anti-GAD67 serum (1:1000, MAB5406; Chemicon), 5% NGS, 0.3% Triton X-100, and 1% bovine serum albumin, overnight at 4° C. After rinsing three times for 10 min each in 0.1% Triton X-100 in PBS, the sections will be incubated with Cy3-conjugated goat anti-mouse antibody (1:1000; Jackson ImmunoResearch, West Grove, Pa.) and 0.0001% DAPI (Sigma-Aldrich, St. Louis, Mo.) in PBS for one hour at room temperature. After a final rinse in PBS for 10 min, sections will be mounted on slides, air dried for at least 30 min, and coverslipped with ProLong Gold antifade reagent (Life Technologies, Grand Island, N.Y.).

Electrophysiology. Whole-cell recordings in the BLA of rats from the in the BLA of rats from the Soman+LY293558+Caramiphen+Midazolam, and control groups will be obtained at 1, 3, and 6 months after soman exposure. Coronal slices (400 µm) containing the BLA will be cut using a vibratome (Leica VT 1200 S; Leica Microsystems, Buffalo Grove, Ill.), in ice-cold cutting solution consisting of (in mM): 115 sucrose, 70 NMDG, 1 KCl, 2 $CaCl_2$, 4 $MgCl_2$, 1.25 $NaH_2PO_4$, 30 $NaHCO_3$. Slices will be transferred to a holding chamber, at room temperature, in a bath solution (artificial cerebrospinal fluid; ACSF) containing (in mM): 125 NaCl, 3 KCl, 1.25 $NaH_2PO_4$, 21 $NaHCO_3$, 2 $CaCl_2$ 1.5 $MgCl_2$, and 20 D-glucose (all purchased from Sigma-Aldrich, St. Louis, Mo.). Recording solution will be the same as the ACSF. All solutions will be saturated with 95% $O_2$, 5% $CO_2$ to achieve a pH near 7.4. Tight-seal (over 1 GΩ) whole-cell recordings will be obtained from principal neurons in the BLA. Spontaneous inhibitory postsynaptic currents (sIPSCs) will be recorded at a holding potential of +30 mV. Ionic currents will be amplified and filtered (1 kHz) using the Axopatch 200B amplifier (Axon Instruments, Foster City, Calif.), digitally sampled (up to 2 kHz) using the pClamp 10.2 software (Molecular Devices, Sunnyvale, Calif.), and further analyzed using the Mini Analysis program (Synaptosoft Inc., Fort Lee, N.J.) and Origin (OriginLab Corporation, Northampton, Mass.).

Behavioral experiments. Animals from the Soman+ LY293558+Caramiphen+Midazolam and control groups will be tested in the open field and the acoustic startle apparatus, 1, 3 and 6 months after soman exposure. In the open field apparatus (40×40×30 cm clear Plexiglas arena), anxiety-like behavior will be assessed as described previously (Aroniadou-Anderjaska et al., 2012; Prager et al., 2014), following the procedure used by Grunberg and collaborators (Faraday et al., 2001). One day prior to testing, animals will be acclimated to the apparatus for 20 min. On the test day, the rats were placed in the center of the open field, and activity will be measured and recorded for 20 min, using an Accuscan Electronics infrared photocell system (Accuscan Instruments Inc., Columbus, Ohio). Data are automatically collected and transmitted to a computer equipped with "Fusion" software (from Accuscan Electronics). Locomotion (distance traveled in cm), total movement time, and time spent in the center of the open field will be analyzed.

Acoustic startle response (ASR) testing will be conducted with the use of the Med Associates Acoustic Response Test System (Med Associates, Georgia, Vt.), which consists of weight-sensitive platforms inside individual sound-attenuating chambers. Each rat is individually placed in a ventilated holding cage. Each cage is placed on a weight-sensitive platform. Subjects' movements in response to stimuli will be measured as a voltage change by a strain gauge inside each platform. Startle stimuli will consist of 120 or 110 dB sound pressure level noise bursts of 20-ms duration. Responses will be recorded by an interfaced Pentium computer as the maximum response occurring during the no-stimulus periods and during the startle period, and will be assigned a value based on an arbitrary scale used by the software of the test system.

Three months after soman-induced SE, animals from the Soman+LY293558+Caramiphen+Midazolam and control groups will be monitored for development of spontaneous recurrent seizures (SRS). The animals will be video-monitored during the 3-month to the 6-month post-exposure period, because this is the time that the chronic phase of epilepsy (persistent SRS) is established after animals have experienced an episode of prolonged SE (Amorin, B O et al. Epilepsy Behav. 2016 Jun. 29; 61:168-173). The frequency of SRS, will be visually scored from videotapes obtained during recording sessions. SRS are characterized by clonic/tonic/tonic-clonic movements of the forelimbs culminating with rearing and falling (stages 3 to 5 according to Racine 1972).

These experiments will confirm the efficacy of the combination therapy (LY293558 administered in combination with caramiphen and midazolam) in preventing neuropathological, pathophysiological, behavioral, and neurological deficits at 30 days, 90 days and 6 months after exposure of adult male rats to soman. At these time points, correlations will be made of anxiety-like behavior and recurrent epileptic seizures with the neuronal and GABAergic interneuronal loss in the BLA, as well as with the level of spontaneous/background GABAergic inhibition in the BLA, a brain region that plays a key role in both emotional behavior and seizure generation.

What is claimed is:

1. A method of treating or reducing the toxic effects of exposure to a nerve agent, or treating or reducing the risks of a neurological condition, comprising administering to a mammalian subject in need thereof:
    (i) an AMPA/GluR5(GluK1) kainate receptor antagonist and
    (ii) an NMDA receptor antagonist, and, optionally, further comprising administering a positive allosteric modulator of synaptic $GABA_A$ receptors to the subject,
    wherein the AMPA/GluR5(GluK1) kainate receptor antagonist and the NMDA receptor antagonist and, optionally, the positive allosteric modulator of synaptic GABA.sub.A receptors, are administered orally or via a route of injection selected from intravenous, subcutaneous, and intraperitoneal.

2. The method of claim 1, wherein the method is for treating a neurological condition selected from epilepsy, seizure, post-traumatic stress disorder, status epilepticus, depression, and anxiety.

3. The method of claim 1, wherein the AMPA/GluR5 (GluK1) kainate receptor antagonist is LY293558.

4. The method of claim 1, wherein the NMDA receptor antagonist is an antimuscarinic compound.

5. The method of claim 1, wherein the NMDA receptor antagonist is caramiphen.

6. The method of claim 1, wherein the optional positive allosteric modulator of synaptic $GABA_A$ receptors is administered.

7. The method of claim 6, wherein the positive allosteric modulator of synaptic $GABA_A$ receptors is a benzodiazepine.

8. The method of claim 6, wherein the positive allosteric modulator of synaptic $GABA_A$ receptors is midazolam.

9. The method of claim 1, wherein the AMPA/GluR5 (GluK1) kainate receptor antagonist is LY293558 and the NMDA receptor antagonist is caramiphen, and the optional positive allosteric modulator of synaptic $GABA_A$ receptors, if administered, is midazolam.

10. The method of claim 1, wherein the AMPA/GluR5 (GluK1) kainate receptor antagonist and the NMDA receptor antagonist and, optionally, the positive allosteric modulator of synaptic $GABA_A$ receptors, are administered by a route of injection selected from intravenous, subcutaneous, and intraperitoneal.

11. The method of claim 1, wherein the AMPA/GluR5 (GluK1) kainate receptor antagonist and the NMDA receptor antagonist and, optionally, the positive modulator of synaptic GABA-A receptors, are administered orally.

12. The method of claim 1, wherein the method is for treating or reducing the toxic effects of exposure to a nerve agent that comprises an organophosphorus toxin.

13. The method of claim 1, wherein the method is for treating or reducing the toxic effects of exposure to a nerve agent that comprises one or more selected from soman and sarin.

14. The method of claim 1, wherein the method is for treating or reducing the toxic effects of exposure to a nerve agent and the subject has been exposed to the nerve agent.

15. The method of claim 1, wherein the method is for treating or reducing the toxic effects of exposure to a nerve agent and the subject is suspected of having been exposed to a nerve agent or is at risk of exposure to a nerve agent.

16. The method of claim 1, wherein the method is effective to treat or reduce the toxic effects of exposure to the nerve agent selected from one or more of seizures, status epilepticus, brain damage, neurological effects, behavioral effects, difficulty breathing, nausea, loss of control of bodily functions, and death.

17. The method of claim 1, wherein the subject is a human adult.

* * * * *